(12) United States Patent
Chakrabarty et al.

(10) Patent No.: US 8,589,082 B2
(45) Date of Patent: Nov. 19, 2013

(54) METHOD FOR MANAGING OBESITY, DIABETES AND OTHER GLUCOSE-SPIKE-INDUCED DISEASES

(76) Inventors: Neilin Chakrabarty, Calgary (CA); Tapantosh Chakrabarty, Calgary (CA)

( * ) Notice: Subject to any disclaimer, the term of this patent is extended or adjusted under 35 U.S.C. 154(b) by 571 days.

(21) Appl. No.: 12/831,238

(22) Filed: Jul. 6, 2010

(65) Prior Publication Data

US 2011/0047108 A1 Feb. 24, 2011

Related U.S. Application Data

(60) Provisional application No. 61/236,062, filed on Aug. 21, 2009.

(51) Int. Cl.
*G06F 19/00* (2011.01)

(52) U.S. Cl.
USPC .......................................................... 702/19

(58) Field of Classification Search
None
See application file for complete search history.

(56) References Cited

FOREIGN PATENT DOCUMENTS

WO WO 2008/154759 * 12/2008

OTHER PUBLICATIONS

Leung et al. "Cardiovascular Disease and Post-prandial Hyperglycemia: A Cardiologist's Perspective", The Federation of Medical Societies of Hong Kong, Medical Bulletin, vol. 15, No. 6, pp. 14-15, Jun. 2010.*
Wu et al., "The Brain in the Age of Old: The Hippocampal Formation is Targeted Differentially by Diseases of Late Life", Annals of Neurology, vol. 64, Issue: 6, pp. 698-706, Dec. 23, 2008.
Gunter et al., "Insulin, Insulin-Like Growth Factor-I, and Risk of Breast Cancer in Postmenopausal Women", Journal of National Cancer Institute, vol. 101, No. 1, pp. 48-60, Jan. 7. 2009.
Donnini et al., "Glucose may Induce Cell Death through a Free Radical-Mediated Mechanism", Biophysics Research Communication, vol. 219, Issue: 2, pp. 412-417, Feb. 15, 1996.
"Study Shows Glucose Consumption Increases Production of Destructive Free Radicals, Lower Level of Key Antioxidant", University of Buffalo News Center, Aug. 16, 2000; http://www.buffalo.edu/news/4839.

* cited by examiner

*Primary Examiner* — Lori A Clow

(57) ABSTRACT

Disclosed is a method for managing diabetes by reducing the post-prandial blood glucose spike, or the glucose shock. The blood glucose spike, or the glucose shock is reduced by generating a person-specific glucose profile for at least one significant meal to tune or train a blood glucose model (kinetic, artificial intelligence or hybrid), and then using the tuned or the trained model embedded in a computation-capable electronic device to compute and recommend a person-specific meal plan and an exercise plan, including semi-continuous meal ingestion and post-meal exercise while sitting at home or office. Advantages over prior art are that the method uses less strenuous exercise with no or less medicine, is person-specific, quantitative and more suitable for use by an individual, a dietician, or a health care practitioner.

19 Claims, 18 Drawing Sheets

METHOD FOR MANAGING OBESITY, DIABETES AND OTHER GLUCOSE-SPIKE-INDUCED DISEASES
(Chakrabarty et al.)
Prior Art:
Three Meals Intake
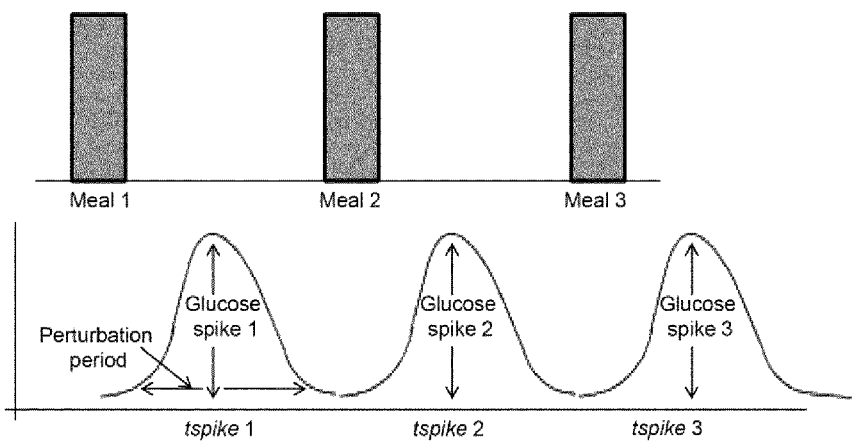
Three Post-prandial
Blood Glucose Spikes
Instant Invention:
Semi-continuous
Meal Intake
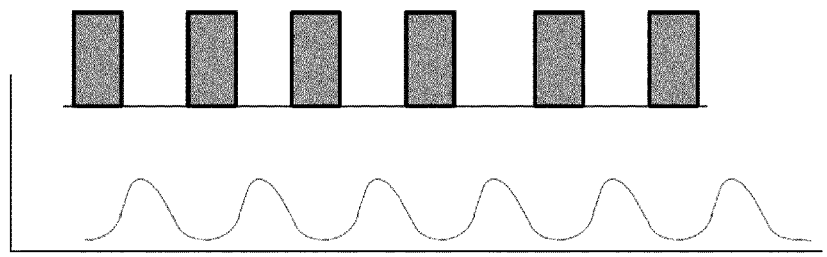
Reduced Post-prandial
Blood Glucose Spikes
FIG. 1

FIG.
12

METHOD FOR MANAGING OBESITY, DIABETES AND OTHER GLUCOSE-SPIKE-INDUCED DISEASES

This application claims the benefits of the provisional application U.S. 61/236,062 filed on Aug. 21, 2009.

CROSS-REFERENCE TO RELATED APPLICATIONS

Not applicable

STATEMENT REGARDING FEDERALLY SPONSORED RESEARCH AND DEVELOPMENT

Not applicable

REFERENCE TO SEQUENCE LISTING, A TABLE, OR A COMPUTER PROGRAM LISTING COMPACT DISC APPENDIX

Not applicable

FIELD OF THE INVENTION

The invention relates to managing obesity, abdominal fat, hair loss, diabetes, other glucose-spike-induced diseases, or adverse health conditions. More specifically, it relates to a person-specific, quantitative method for reducing post-prandial glucose spike to lower the risk of developing, or if already developed, to manage the said diseases or health conditions.

BACKGROUND OF THE INVENTION

A spike in blood glucose level occurs following each significant meal: breakfast, lunch or dinner, as the carbohydrates in a meal convert to glucose and the glucose from the blood stream enters the cells. A glucose spike is defined as the highest blood glucose level after a meal minus the pre-meal glucose level. Resulting from a step input of carbohydrates to the human digestive system, a post-prandial or post-meal glucose spike may occur following breakfast, lunch or dinner, causing three spikes and three perturbation periods (top half of FIG. 1). A perturbation period is defined as the post-meal time period during which the blood glucose level increases above the pre-meal level, going through a maximum before approaching the pre-meal glucose level. The increase in area under the glucose concentration vs. time plot in the perturbation period over the pre-meal area can be taken as a measure of the glucose shock experienced by the vital organs and systems in the body.

The time of occurrence of the glucose spike (tspike), as shown in FIG. 1, and its amplitude, defined as the maximum increase in glucose level over the pre-meal glucose, depend on the type and amount of carbohydrates ingested, a person's metabolism and insulin delivery system.

The body cells need glucose for energy, but higher than normal level of glucose in the blood imparts a glucose shock that may lead to adverse health conditions or life-threatening diseases, including but not limited to, obesity, abdominal fat, hair loss, pre-diabetes, diabetes, hypoglycemia, cardiovascular diseases, aging, Alzheimer's disease, dementia, free-radical-related diseases, or cancer.

Obesity is becoming a significant health risk all over the world. In the USA, 31% of the population is considered obese and 300,000 deaths annually are linked to obesity. Obesity is measured by the percentage of the body weight that is fat. Men with more than 25 wt % body fat, and women with more than 30 wt % body fat are considered obese. Obesity is also measured by the body mass index (BMI), which is defined as the body weight in kilograms by the square of height in meters. A person with a BMI of 30 or more is considered obese. There is a strong correlation between obesity and the occurrence, of Type 2 diabetes. Obesity in mid-life increases the risk of developing Alzheimer's disease by a factor of 3.5. Moreover, abdominal fat in obese or non-obese people is linked to diabetes and cardiovascular diseases like heart attack and stroke. Elevated lipids (fats) in the blood also damage beta-cells that produce insulin needed for glucose uptake by cells. There then is a need for a method for managing obesity and reducing abdominal fat.

Diabetes, caused by high blood glucose level in the blood stream, is a serious illness affecting close to 28 million in the USA and 250 million worldwide. About 50 million in the USA are pre-diabetic. Blindness, kidney disease (nephropathy), nerve damage (neuropathy), stroke, heart attack, and leg amputation are some of the menaces of diabetes. Every year millions succumb to cardiovascular complications resulting from diabetes. Disease of the retina (retinopathy), caused by diabetes, is the main cause of sight loss in working age adults. There then definitely is a need for a method for lowering the risk of developing diabetes, or managing diabetes, if already developed.

Blood glucose level is controlled by insulin, a hormone released by the pancreas into the blood. From the blood, the insulin enters the cells, from where it brings the glucose receptors (GLUT-4) to the cell membranes that are in contact with the blood stream. It is through the GLUT-4 that the blood glucose enters the cells.

In a Type 1 diabetic patient, insulin is not produced, necessitating the injection of synthetic insulin as a life-saving measure. In a Type 2 diabetic patient, insulin is not produced in sufficient amounts, or the body cells resist the absorption of insulin—a condition known as insulin resistance—both of which may lead to inefficient glucose uptake by the body cells, causing a condition termed as impaired glucose tolerance (IGT). IGT raises the blood glucose above the normal level of 6 mmol/L, measured after 12-hour of fasting. Two units are used for the blood glucose level: mmol/L (used in Canada, Europe, India, and China) or mg/dL (used in USA). A multiplication by 18 of the blood glucose level number in mmol/L is needed to obtain the glucose level in mg/dL.

To manage Type 2 diabetes, the prior art guidelines recommend monitoring the 12-hour fasting and the two-hour after-meal blood glucose levels. These guidelines, however, fail to recognize the adverse long-term effects of exposing the vital body organs and systems to a glucose spike or a glucose shock occurring within the first two hours of taking a meal.

The high blood glucose level in Type 2 diabetes is controlled through medicine (prescribed or alternative), exercise, and diet. Some medicines may have adverse health effects on some patients. The exercise and the diet plans recommended by prior art are general guidelines that do not take into account a person's carbohydrate intake, body metabolism and insulin delivery system. What may work for one person may not work for another. These general guidelines recommend taking low glycemic index (GI) and low glycemic load (GL) food, and performing exercise, but do not provide any quantitative method for tailor-making a meal plan or an exercise plan for an individual. The term glycemic index (GI) is defined as the potential of a food item to raise the blood glucose level relative to that by 100% glucose. The term glycemic load (GL) for a food item is defined as the product of GI of the item and its carbohydrate content in grams. The prior art guidelines do not recommend the reduction of post-prandial glucose spike or glucose shock, nor do they recommend performing post-prandial exercise as a way of controlling the glucose spike or glucose shock. There then is a definite need for a person-specific, quantitative method for lowering the risk of developing, or if already developed, managing, diabetes, using less or no medicine.

Hair loss or hair thinning in diabetic patients has been linked to high blood glucose that restricts the blood flow and nutrients supply to the hair roots and follicles. Although not a life-threatening health condition, hair loss can cause a significant psychological distress, especially to women.

Elevated blood glucose level may also accelerate aging-related diseases, including but not limited to, cognitive or memory decline. For example, memory decline has been linked to elevated glucose level by researchers from the Taub Institute for Research on Alzheimer's disease and the aging brain at Columbia University Medical Center. These researchers found that elevated blood glucose adversely affects the dentate gyrus, a sub region of the hippocampus, which is a delicate brain structure vital to human memory (WU et al., "The Brain in the Age of Old: The Hippocampal Formation is Targeted Differentially by Diseases of Late Life", Annals of Neurology, Vol.: 64, Issue: 6, pages: 698-706, Dec. 23, 2008). The risk of developing Alzheimer's disease, an aging-related disease, increases by a factor of 3.5 and 2, respectively, with obesity and diabetes, both of which are linked to elevated blood glucose levels. Aging-related diseases affect the wellness of a person, while placing an enormous psychological and financial burden on families and the health care system. There is a need for reducing the risk of developing aging-related diseases caused by elevated blood glucose levels.

Body's inability to absorb insulin secreted by the pancreas in response to the post-prandial glucose spike may lead to elevated blood insulin level that may adversely affect the functions of the vital organs and systems, including promotion of cellular growth or cancer. A study by researchers at Albert Einstein College of Medicine of Yeshiva University found that higher-than-normal levels of insulin place post-menopausal women at an increased risk of breast cancer (GUNTER et al., "Insulin, Insulin-Like Growth Factor-I, and Risk of Breast Cancer in Postmenopausal Women", Journal of National Cancer Institute, Vol.: 101, No.: 1, pages: 48-60, Jan. 7, 2009). Elevated insulin level also decreases DHEA (dehydroepiandrosterone), a hormone that is conducive to longevity, and may increase beta-amyloid, a protein that builds up in the brains of patients with Alzheimer's disease. Elevated blood glucose level is also linked to Alzheimer's disease. Hence there is a need for reducing high insulin level in the blood by controlling the post-prandial glucose spike or glucose shock.

Blood glucose may also generate free radicals linked to cell abnormalities, including cancer (DONNINI et al., "Glucose may Induce Cell Death through a Free Radical-Mediated Mechanism", Biophysics Research Communication, Vol.: 219, Issue: 2, pages: 412-417, Feb. 15, 1996).

Post-prandial glucose spike may also cause reactive hypoglycemia. Hypoglycemia is a condition in which excessive insulin release by the pancreas in response to a glucose spike leads to a dangerously low glucose level in the blood. Heart fibrillation, dizziness, tremors and coma are some of the ill effects of hypoglycemia. Eating more carbohydrates to raise the sugar level may be a quick fix, which in the long run may be detrimental to the pancreas and other organs. There then is a need for a more effective method of managing hypoglycemia.

Elevated blood glucose level measured two hours after a meal may cause cardiovascular diseases even in non-diabetic patients whose fasting glucose level is normal (LEUNG, "Cardiovascular Disease and Post-prandial Hyperglycemia: A Cardiologist's Perspective", The Federation of Medical Societies of Hong Kong, Medical Bulletin, Vol.: 15, No.: 6, Pages: 14-15, June 2010). Since the post-prandial glucose maximum may be higher than the glucose level at two hours after a meal, the risk of cardiovascular diseases in non-diabetic patients subjected to post-prandial glucose spike may be even higher than that reported by Leung. Diabetic patients are even more susceptible to cardiovascular diseases. There is a need for controlling blood glucose spike or glucose shock to lower the risk of cardiovascular diseases in diabetic or non-diabetic patients.

The background information underscores the need for a person-specific, quantitative method for reducing blood glucose spike or glucose shock to lower the risk of developing, or to manage, if already developed, the various glucose-spike-induced diseases and adverse health conditions. The instant invention provides such a method for lowering the risk of developing, or managing, if already developed, diseases, including but not limited to, obesity, abdominal fat, pre-diabetes, diabetes, hypoglycemia, aging, cardiovascular diseases, or cancer.

The invention culminated from an adversity when one of the inventors was initially alerted about being pre-diabetic and later diagnosed with Type 2 diabetes, because of higher than normal 12-hour fasting glucose level and symptoms of numbness in fingers, toes and around the skull. Having just completed 13 consecutive marathons—training regularly and running at least one marathon a year—over 10 years, the runner was shocked to realize that the prior-art-prescribed meal plan and the strenuous physical activities fell short in keeping the blood glucose level within a normal range.

The invention was conceived of when the human digestive system, a complex reactor, was compared with a simpler industrial reactor. An industrial reactor is fed at a constant injection rate to ensure target product rate and quality, and to avoid adverse reactor conditions, such as temperature excursion, reactor damage, or even reactor shutdown. By contrast, the complex human digestive system is fed in three step functions through three significant meals: breakfast, lunch and dinner, subjecting the system to three post-prandial glucose spikes or glucose shocks, and three glucose perturbation periods (top half of FIG. 1). These spikes or shocks repeated daily since childhood may lead to various adverse health conditions or life-threatening diseases.

As described in Examples 1 and 2 later in this disclosure, by controlling the post-prandial glucose spike or glucose shock following the method of this invention, the runner was able to lose body weight and abdominal fat, bring down blood glucose level from the Type 2 diabetic level to the normal range, and assuage some symptoms of aging.

BRIEF SUMMARY OF THE INVENTION

It is an object of the invention to provide a quantitative, person-specific method for reducing the post-prandial blood glucose spike or glucose shock to lower the risk of developing, or, if already developed, manage glucose-spike-induced diseases or adverse health conditions, including but not limited to, obesity, abdominal fat, pre-diabetes, diabetes, hypoglycemia, hair loss, aging, dementia, Alzheimer's disease, cardiovascular diseases, nephropathy, neuropathy, retinopathy, or cancer.

It is yet another object of the invention to provide a method that can be implemented in a computation-capable electronic device for use by an individual, heath care professionals, nutritionists or dieticians.

It is yet another object of the invention to provide a machine that can be used to perform post-prandial body movement while sitting in a chair at home or at work.

In its broadest concept, the invention controls the blood glucose spike or glucose shock to be within a target range by treating the human digestive system as an industrial reactor, feeding the human reactor semi-continuously (bottom half of FIG. 1) by splitting at least one significant meal into more than one portion and taking each portion at a different time, and/or by performing post-prandial exercise to increase the glucose uptake from blood. The method comprises the steps of generating, though measurements, a person-specific blood glucose profile for at least one significant meal; using the said profile to tune or train a blood glucose response model; and using the said tuned model to recommend a person-specific meal plan and an exercise plan, which when followed keep the blood glucose spike or glucose shock to a target range. By keeping the post-prandial blood glucose spike or glucose shock within a target range, the method lowers the risk of developing, or to manage, if already developed, glucose-spike-induced diseases or adverse health conditions, including but not limited to, obesity, diabetes, hair loss, aging, dementia, Alzheimer's disease, cardiovascular diseases, nephropathy, neuropathy, retinopathy, or cancer. Semi-continuous feeding is accomplished in the invention by meal splitting, which is defined as dividing a meal (e.g., breakfast) into several portions and taking each portion at a different time. Unlike prior art, an important aspect of the invention is to perform exercise after a meal to more effectively reduce the post-prandial glucose spike or glucose shock.

In one embodiment, semi-continuous feeding is accomplished by sipping at least a portion of at least one meal as a liquid from a bottle, or by administering the liquid food through a feeding tube to a patient.

In another embodiment, semi-continuous feeding is accomplished by eating at least a portion of at least one solid meal over a longer period of time.

The invented method comprises generating a person-specific blood glucose profile (concentration vs. time) for at least one significant meal, identifying the time to reach the glucose spike (tspike); determining the glucose spike or the glucose shock; developing a kinetic model or an artificial intelligence model or a hybrid model; tuning the model with a person-specific glucose profile; embedding the model in a computation-capable electronic device; and then programming the device to recommend a meal plan, including a meal splitting plan, and an exercise plan, including the timing of the commencement of the post-prandial exercise to control the post-prandial glucose spike or glucose shock within a target range.

In one embodiment of the invention, the meal splitting and post-prandial exercise plans are combined with a meal choice to control the blood glucose level within the first two hours of at least one significant meal. The meal choice includes a meal combination with relatively low glycemic indices (GI) and glycemic load (GL) values—meeting the daily recommended carbohydrate and protein needs. The split meals are taken 30 to 120 minutes apart. The exercise is commenced at a time t that falls between (tspike−x) minutes and (tspike+y) minutes, where x is from 15 to 30 minutes and y is from 15 to 60 minutes.

In another embodiment of the invention, a kinetic model is used to develop an equation relating the blood glucose concentration to: carbohydrates ingested, the time since meal, the rate constant for the carbohydrates to glucose conversion reaction, and the rate constant for the glucose uptake by the cells. The model is personalized by tuning it with the blood glucose concentration vs. time data for each person measured after at least one significant meal. The tuned kinetic model is then used to develop a meal plan (type of food, amount of carbohydrates and meal splitting) and an exercise plan (type of exercise, frequency, start time since meal, and duration of exercise), which when followed keep the post-prandial glucose spike, or the glucose shock within a target range. The exercise plan includes body movement, leg movement sitting in a chair, forward or backward walking or running, weight training, dancing, using a vibration machine, using a tread mill, an elliptical machine or a rowing machine, spot running, stair climbing, or any other suitable form of physical activity.

In yet another embodiment of the invention, the post-prandial glucose spike, or the glucose shock is reduced by using a leg exerciser that allows up and down, circular or elliptical movements of at least one leg, while sitting in a chair at home or at work in an office.

In yet another embodiment of the invention, the post-prandial glucose spike, or the glucose shock is reduced by using a machine that vibrates at least one leg, while sitting in a chair at home or at work in an office.

In another embodiment of the invention, an artificial intelligence (AI) model is trained with the blood glucose concentration vs. time data measured for each person after a significant meal. The personalized AI model is then used to develop a meal plan and an exercise plan, which when followed keep the post-prandial glucose spike, or the glucose shock within a target range.

In yet another embodiment, any other suitable model is tuned or trained to develop a meal plan and an exercise plan, which when followed keep the post-prandial glucose spike, or the glucose shock within a target range. For example, a hybrid model comprising the kinetic model and the artificial intelligence model may be used.

In yet another embodiment of the invention, the method is embedded in a computation-capable electronic device, including but not limited to, a personal desktop computer, a laptop computer, a workstation, a Smartphone, or a glucose level monitor, each of which is equipped with data storage, computation and display capabilities to: store personal data (age, height, weight, gender, body frame size), food (GI, GL, carbohydrates content), and personal glucose profile data; compute the steps associated with tuning or training a blood glucose response model; and display the recommended meal and exercise plans to lower the amplitude of each post-prandial glucose spike, or the glucose shock.

In yet another embodiment of the invention, the measured glucose profile alone may be used without using a computation-capable device to develop a meal plan and a post-meal exercise plan.

In yet another embodiment, the method is used to lower the risk of developing, or to manage, if already developed, obesity or abdominal fat.

In yet another embodiment of the invention, the method is used to lower the risk of developing, or to manage, if already developed, pre-diabetes and diabetes.

In yet another embodiment, the method is used to manage hypoglycemia.

In yet another embodiment, the method is used in combination with a Type 1 or Type 2 diabetes medicine (prescribed or alternative), including insulin, to reduce the medicine dosage.

In yet another embodiment, the method is used to assuage the symptoms of aging, including but not limited to, cognitive decline, dementia, Alzheimer's disease, cancer, or cardiovascular diseases by reducing the glucose spike or the glucose shock.

The advantages of the invention over prior art include an individualized, quantitative method for more effective reduction of the post-prandial glucose spike, or the glucose shock, lowering the risk of developing or managing, if already developed, obesity, abdominal fat, pre-diabetes, diabetes, hypoglycemia, hair loss, aging, cardiovascular diseases, nephropathy, neuropathy retinopathy, or cancer—with less or no medicine.

BRIEF DESCRIPTION OF THE DRAWINGS

FIG. 1 shows three significant glucose spikes or glucose shocks appearing after three significant meals (the top half of the figure); and six reduced glucose spikes appearing after six semi-continuous meals (the bottom half of the figure).

DETAILED DESCRIPTION OF THE INVENTION

Figure 2:
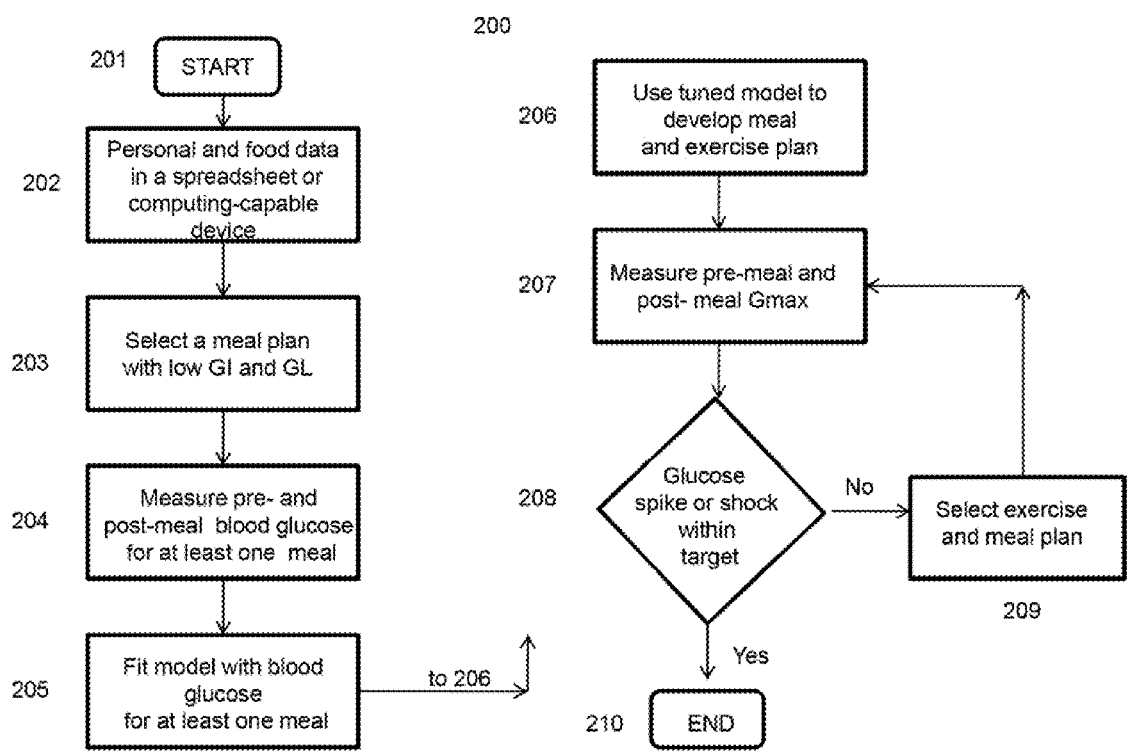
FIG. 2 is a flow diagram of a method for controlling glucose spike, or glucose shock according to one embodiment of the invention.

The method for reducing the post-prandial glucose spike, or the glucose shock to manage obesity, abdominal fat, diabetes, aging and other glucose-spike-induced diseases, according to this invention, comprises the steps of:
  a) generating, through measurements, a person-specific profile of glucose concentration vs. time for each significant meal, each profile indicating the timing, the glucose spike or the glucose shock;
  b) tuning or training a blood glucose response model with the measured person-specific blood glucose profile data for at least one significant meal;
  c) using the tuned or trained blood glucose response model to develop each significant meal plan, including semi-continuous meal taking including splitting at least one meal, and a post-prandial exercise plan needed for reducing the post-prandial glucose spike or the glucose shock, defined by the area under the blood glucose concentration vs. time plot, to a target level; and
  d) executing the meal and/or the post-prandial exercise plan and comparing the measured glucose spike with a target spike, or by comparing the area under the blood glucose vs. time plot with a target area to assess the success of the glucose spike reduction plan, and readjusting, if necessary, the meal and/or the post-prandial exercise plan using the tuned or trained blood glucose response model.

The invention, in sharp contrast to teachings of the prior art, recommends post-prandial or post-meal exercise within a specified time range to reduce the blood glucose spike or the glucose shock. This is a significant improvement over prior art as it allows achieving more glucose spike or glucose shock reduction by doing less exercise at the right time. As illustrated in Example 5, for managing high blood glucose, moderate physical activity after a meal is superior to strenuous physical activities before a meal, or starting at two to three hours after a meal, as recommended by the prior art. Post-prandial exercises, according to this invention, may include body movement, forward or backward walking or running, weight training, dancing, using a vibration machine, a treadmill, an elliptical machine or a rowing machine, spot running, stair climbing, or any other suitable form of physical activity. In yet another embodiment of the invention, the post-prandial glucose spike, or the glucose shock is reduced by using a machine that vibrates at least one leg, while sitting in a chair at home or at work in an office.

In one embodiment of the invention, the post-prandial glucose spike, or the glucose shock is reduced by using a leg exercise machine that allows up and down, circular or elliptical movements of at least one leg, while sitting in a chair at home or at work in an office.

In yet another embodiment of the invention, the post-prandial glucose spike, or the glucose shock is reduced by using a machine that vibrates at least one leg, while sitting in a chair at home or at work in an office.

In practicing the invention, a meal combination with relatively low glycemic indices (GI) and glycemic load (GL) values—meeting the daily recommended carbohydrate and protein needs—may be selected.

Also in practicing the invention, the meals may be taken semi-continuously by splitting at least one meal into different portions and taking each portion at a different time, with the portion amount and time of ingesting chosen such that the post-prandial glucose spike or the glucose shock is controlled to a target range. As shown qualitatively in the bottom half of FIG. 1, semi-continuous eating by meal splitting reduces the post-prandial glucose spikes or glucose shocks. Semi-continuous feeding may also be accomplished by sipping at least a portion of at least one significant meal as a liquid from a bottle, the said liquid containing protein and carbohydrates in a ratio suitable for good nutrition as well as for reducing the glucose spike or the glucose shock. Semi-continuous or continuous feeding may be accomplished by pumping the liquid food through a feeding tube to a patient.

The maximum post-prandial blood glucose level or the glucose spike is reduced to be not more than 2 to 5 mmol/L above the pre-meal blood glucose level. Alternatively, the area under the blood glucose concentration vs. time plot in the post-meal perturbation period—after subtracting the area corresponding to the pre-meal glucose level over the same period—is reduced by at least 20% over the area before following the method. By reducing the area, which is a measure of the glucose shock (unit of mmol/L·minutes), the glucose shock to vital organs and systems is reduced. Reduced glucose shock lowers the glucose-shock-induced health risks.

In one embodiment, the method is used to lower the risk of developing, or, if already developed, manage obesity or reduce abdominal fat.

In another embodiment, the method is used to lower the risk of developing, or, if already developed, manage pre-diabetes and Type 1 or Type 2 diabetes. The method may be used without or with prescribed medicine, including insulin or alternative medicine with the object of tapering the medicine dosage with time.

In yet another embodiment, the method is used to manage hypoglycemia by controlling post-prandial glucose spike or glucose shock. In so doing, it prevents the insulin release from going to an "overdrive" and reducing the blood glucose to a dangerously low level, causing dizziness, fibrillation of heart and even coma.

In another embodiment of the invention, the method is used to lessen hair loss caused by high blood glucose level.

In yet another embodiment, the method is used to manage aging by controlling glucose spike or glucose shock and associated high insulin levels that may adversely affect the vital organs and systems, and may lead to cancer. Reducing post-prandial glucose spike or glucose shock, according to the instant invention, may increase longevity, delay aging and reduce cancer risk.

In another embodiment of the invention, the method is used to reduce the risk of developing cardiovascular diseases in diabetic or non-diabetic patients, by controlling post-prandial glucose spike or glucose shock.

In yet another embodiment of the invention, the method is used to reduce the risk of developing retinopathy, nephropathy or neuropathy in prediabetic, diabetic or non-diabetic patients, by controlling post-prandial glucose spike or glucose shock.

Furthermore, in practicing the invention, a computer, a Smartphone or a glucose level monitor may be used for storage of personal blood glucose profile, blood glucose response model, tuning or training of model, and computing and displaying recommended meal and exercise plans.

The blood glucose response model in the invention is a kinetic model for the reactions carbohydrates to glucose to glucose uptake by body cells, an artificial intelligence (AI) model, or a hybrid model comprising a kinetic model and an AI model.

In another embodiment, the glucose profile may be used alone without using any tuned or trained model to develop a meal plan and a post-meal exercise plan to reduce glucose spike or glucose shock for the purpose of lowering the risk of developing, or, if already developed, managing obesity, abdominal fat, diabetes, or hypoglycemia.

In FIG. 2, a flow diagram of the method, according to one embodiment of the invention, is shown. The method 200 includes generally a plurality of steps or blocks that may be performed serially. The steps shown are for illustration only and the order of one or more steps may be changed, omitted or added without deviating from the scope and the spirit of the invention. The method starts at step 201.

In step 202, personal information and food data are entered either in a spreadsheet or in a program embedded in a computation-capable electronic device. The personal information includes age, sex, height, weight, and the frame size of the person, for whom the meal plan and the exercise plan are being developed. The food data may include the food eaten by the person for breakfast, lunch or dinner. The glycemic indices (GI) and glycemic loads (GL) of these foods are also entered either directly or calculated using prior art correlations or retrieved from a look-up table in the program written for the electronic device. In step 202, the blood volume and the body mass index (BMI) are calculated from known correlations. The daily recommended carbohydrate needs (DRCN) and protein needs are also calculated from prior art using age, gender, height and weight of a person.

In step 203, a number of food choices are entered for each significant meal: breakfast, lunch or dinner. These may advantageously be foods with low GIs and low GLs. Protein is incorporated advantageously in each meal to suppress the rate at which carbohydrates are converted to glucose. The subtotal amount of carbohydrates for each significant meal is calculated separately and added up for three significant meals—including those for snacks—to make sure that total is close to the DRCN for the person. The total protein in all meals should also be close to the recommended protein need for the person.

In Step 204, the blood glucose levels are measured before a significant meal is taken and at different times for at least up to two hours after a meal, either intermittently or continuously. The measurements may be made by the person at home using a glucose monitor or by a health care professional in a certified laboratory. The measurements may be used to generate a plot of glucose level vs. time using the spreadsheet or the program embedded in the computation-capable electronic device. From this plot, the maximum glucose level (or glucose spike) and the time at which the spike (tspike) occurs are recorded. The area under the glucose level vs. time plot may also be calculated to determine the glucose shock by subtracting from the said area the base area corresponding to the pre-meal glucose concentration over the same period.

According to one embodiment of the invention, in step 205, the measured glucose data are used to tune the glucose kinetic model for the reactions of carbohydrates (C) to glucose (G) to glycogen (GLY) and energy (E) and is shown by equation 1 below for the two-step reactions:

$$C \rightarrow G \rightarrow GYL \text{ and } E$$

that yields a mathematical expression for the kinetic model relating the blood glucose level at any time t since taking a meal with three measurable or known factors and three tunable parameters, the said kinetic model is as shown by equation 2 (the kinetic model with three measurable or known factors: Go, Co and BV, and three tunable parameters: CMW, k1 and k2):

$$G = Go + 1000*(Co/CMW)/BV)*[k1/(k2-k1)]* [\exp(-k1*t) - \exp(-k2*t)]$$

where, G is the blood glucose concentration at any time following a meal, in mmol/L;
Go is the blood glucose concentration prior to taking a meal, in mmol/L;
Co is carbohydrate ingested during a meal, in g;
BV is the blood volume of the person, in liters;
CMW is a meal-specific tunable parameter representing the average molecular weight of the carbohydrates ingested during a meal, in g/mol;
k1 is a person-specific tunable parameter representing the rate constant for the reaction C→G, in $min^{-1}$;
k2 is a person-specific tunable parameter representing the rate constant for the reaction G→GLY and E, in $min^{-1}$;
t is the time from the start of the most recent meal, in min;
wherein the said kinetic model is tuned with the person-specific glucose profile data to determine the best-fit or the tuned values of CMW, k1 and k2, and which values are then used along with pre-meal Go, Co ingested, and BV to calculate:

(1) the G in blood level at any time following a meal using the kinetic model;
(2) the tspike, the time to reach the glucose spike using the best-fit or the tuned values of k1 and k2 from equation 3 below:

$$t\text{spike}=[1/(k1-k2)]*\ln(k1/k2);$$

(3) the glucose spike (Gmax) using the best-fit or the tuned values of CMW, k1 and k2, and the known values of Go, Co and BV from equation 4 below:

$$G\text{max}=Go+1000*((Co/CMW)/BV)*[k1/(k2-k1)]*[\exp(-k1*t\text{spike})-\exp(-k2*t\text{spike})]; \text{ and}$$

(4) the glucose shock by subtracting the base area (corresponding to the pre-meal) from the area under post-meal G vs. t plot, over the same period; and wherein at least one of which calculated values (G, tspike, Gmax or glucose shock) is used to develop a meal plan and or a post-prandial exercise plan to keep the glucose spike, or the glucose shock following a meal within a target level, for the purpose of lowering the risk of developing blood-glucose-spike-induced diseases, or managing the said diseases, if already developed.

Equation 2 (the kinetic model) shows that the blood glucose concentration (G) is dependent on the pre-meal blood glucose concentration (Go), the total carbohydrates ingested (Co), the time since meal (t), the BV, and the CMW (a meal-specific tunable parameter), and the two person-specific tunable parameters: k1 and k2. The higher the pre-meal blood glucose (Go), the higher is the post-prandial glucose level for a given intake of carbohydrates. The blood glucose level (G) also increases with the amount of carbohydrates intake (Co). The blood glucose level is also time dependent, initially increasing with time as the carbohydrates convert to glucose and then decreasing with time as the glucose uptake from blood by the body cells increases by the action of insulin. Thus a maximum in glucose concentration occurs at a certain time. The time to reach the maximum glucose concentration or glucose spike (tspike) is given by equation 3 above.

Equation 3 shows that tspike is dependent on k1 and k2 only and not on Go or Co. The tspike increases with a decrease in k1, which is achievable by eating slower-digesting carbohydrates. Including protein in a meal may also lower K1.

The maximum blood glucose concentration (Gmax) is given by equation 4 above, which uses the best-fit or the tuned values of CMW k1 and k2, and the known values of Go, Co and BV.

Equation 4 shows that, for a given meal, lower Gmax can be achieved by splitting the meal to reduce Co and taking each split meal at more than one time. The incorporation of protein in the meals may also reduce Gmax by lowering k1. Properly timed post-meal exercise may help reduce Gmax by making k2 higher or burning more calories.

Equation 2 is fitted in step 205 with measured glucose level data for at least one meal from step 204 to obtain the least-squares estimates or the best-fit values of CMW, k1 and k2.

In step 206, the tuned model is used to develop a personalized meal plan and an exercise plan to lower the postprandial glucose spike or glucose shock to be within a target range. The glucose spike reduction for a chosen meal plan and an exercise plan may be calculated using equation 4. The glucose shock reduction for a given meal plan and an exercise plan may be calculated by generating model-predicted glucose concentrations at different times using equation 2, plotting the generated glucose concentrations vs. time data, calculating the area under the curve in the perturbation period, and subtracting from the said area the base area corresponding to the pre-meal glucose concentration over the same period. The tuned model can be used advantageously to calculate the number of meal splits and the amount of carbohydrates to be taken with each split meal. The tuned model can also be used to develop an exercise plan to reduce the glucose spike or glucose shock by a certain percentage. For example, if a 20% reduction in glucose spike or glucose shock is desired, then the calories intake through food may be reduced roughly by 20%, or the calories burnt by exercise may be increased roughly by 20%. Available literature data for calories intake from food and calories burnt by different types of exercises are included in the computer program or in a spreadsheet that is embedded in the computation-capable electronic device. Relationship is also available in the literature for converting calories to equivalent carbohydrates (4 calories=1 gram carbohydrates). Exercises are chosen from body or leg movement, forward or backward walking or running, weight training, dancing, using a vibration machine, spot running, stationary or non-stationary biking, stair climbing, or any other suitable form of physical activity. Backward walking or running may be incorporated advantageously in the exercise plan to reduce the amount of time needed to burn the same number of calories and to reduce the impact of exercise on the knees. Backward walking can also be used during rehabilitation from an injury that precludes forward walking. Using a vibration machine while standing, sitting or laying may also be used to reduce glucose spike or glucose shock. Unlike prior art, the method of the instant invention calls for performing exercise within two hours of a meal, which is more beneficial than pre-meal exercise or exercise done two hours after a meal, as described in Example 1.

In step 207, a pre-meal glucose level is measured after which the recommended meal from step 206 is eaten and/or the recommended exercise from step 206 is completed. The blood glucose level is then measured at a time close to the tspike from step 204 to determine the glucose spike reduction. Alternatively, the blood glucose levels are measured at different times up to at least 2 hours since taking a meal, and plotted to determine the glucose shock reduction.

In Step 208, the glucose spike measured in step 207 is compared with the target glucose spike range. Alternatively, the glucose shock determined from step 207 is compared with the target shock. If the glucose spike or the glucose shock is within the target range, then acceptable the meal and the exercise plans have been established, ending the method execution at step 210. The glucose spike should be no more than 2 to 5 mmol/L above the pre-meal glucose level. The glucose shock should be at least 20% lower than that before following the method of this invention. The target range for the blood glucose spike or the glucose shock may be set after consultation with a health care professional.

If the glucose spike or the glucose shock is above the target range, the method goes to step 209, where a new meal plan with reduced meal splitting, and an exercise plan with higher intensity are selected. From there, one is directed to step 207 and then to step 208. A few such iterations may be necessary to reach an effective meal and an exercise plan to lower the glucose spike or glucose shock to a target range. The method is robust enough that food items not selected in tuning the model may also be incorporated by matching their GI values.

One of ordinary skill in the art may realize that the model may need retuning from time to time as practicing the method may correct the insulin resistance, which may make the meal or the exercise plan less restrictive.

In one embodiment of the invention, the kinetic model is fitted with measured glucose level by regression. In yet another embodiment, an artificial intelligence (AI) model is trained in step 205 using experimental data from step 204. The trained model then develops an exercise plan and a meal plan to limit the glucose spike or the glucose shock within a target range. In yet another embodiment, a hybrid model, comprising a kinetic model, an AI model or any suitable model is tuned or trained in step 205 using experimental data from step 204.

In practicing the invention, one of ordinary skill may find it advantageous to use a glucose level monitoring device and a computation-capable electronic device. The glucose level monitoring device may comprise at least one lancet to create a blood droplet on a finger tip, the palm or an arm. A test strip may be pushed into a small entry point to the monitor. The strip code number should match with that displayed in the monitor. The other end of the strip then may be brought to the base of the blood droplet which enters the monitor through a small channel by capillary action for glucose level measurement. The measured glucose level in the blood may be displayed in the monitor. It may be advantageous if the monitor is checked for accuracy using a control solution of known glucose concentration, as supplied by the manufacturer.

Alternatively, the blood glucose level may be monitored by a health care professional by drawing blood at different times and having it analyzed in a certified laboratory. Yet another way of measuring the glucose level may be through continuous measurement by inserting a needle under the skin, or placing a measuring device in contact with the skin.

Figure 3:
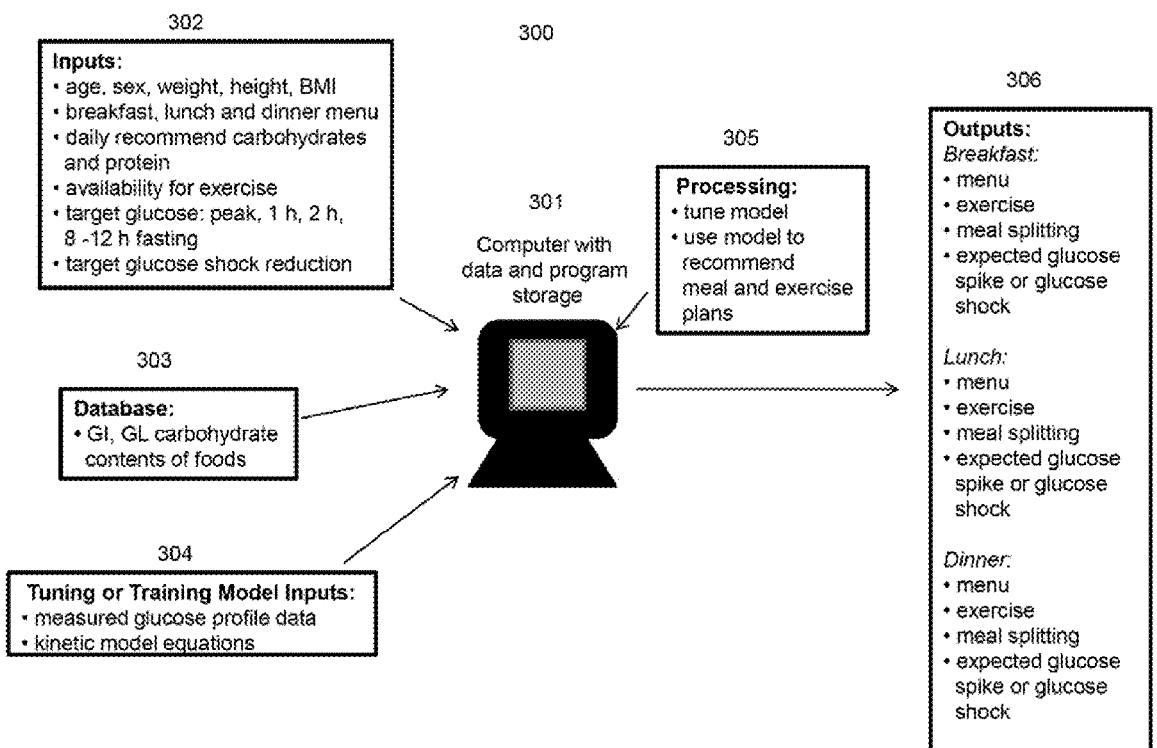
FIG. 3 is a block diagram showing the embedding of the method of the invention in a computer.

FIG. 3 illustrates how the method 200 can be implemented in a computing environment 300. The computer 301 can be a laptop, a personal computer, a workstation, a computer with multiple users (a networked computer), or a computer with access to Internet. The computer may have external or internal disk storage devices (hardware). Software with a set of instructions is developed and embedded in the computer. The software and the hardware work together to tune or train the blood glucose model. The tuned or the trained model is used to recommend a meal and a post-prandial exercise plan for each significant meal.

The inputs 302 may include, but not limited to, personal information (age, sex, weight, height, body frame size, BMI), which may be used to calculate the blood volume and the daily recommended carbohydrate need and protein need of the person for whom the plan is being developed. The inputs may also include preferred breakfast, lunch and dinner menus for the individual. The inputs also include if time is available for exercise on a given day for a given meal. Inputs also include the target blood glucose levels at different times and target glucose shock reduction.

In practicing the invention, the computing environment 300 may also advantageously use existing databases 303 from the literature and store them in the computer 301. These databases contain data, including but not limited to, on GI, GL, and carbohydrate contents of different food items.

The computing environment 300 uses inputs for tuning or training the blood glucose model, as shown in box 304 in FIG. 2. These inputs may comprise measured glucose profile data of an individual after each significant meal. The significant meal may include breakfast, lunch and dinner. Having one profile for each meal may be advantageous as the food intake and metabolism may vary from morning to afternoon to evening. In addition to the personal glucose profile data for each meal, the computing environment 300 also needs the kinetic model equations (equations 2, 3, 4 and 5).

Box 305 is the processing section of the method in a computing environment 300, where the tuning and/or training of the model as well computation takes place to recommend the meal plan and the exercise plan to achieve a target glucose spike or glucose shock.

Box 306 is the output section of the method in the computing environment 300. The outputs are stored in memory for display or plotting. The outputs may be grouped by each significant meal. For each meal, the outputs may include the meal menu, exercise plan, meal splitting, and expected glucose spike or glucose shock. The outputs may also include the historical measured glucose concentration in a tabular format or as a plot.

Figure 4:
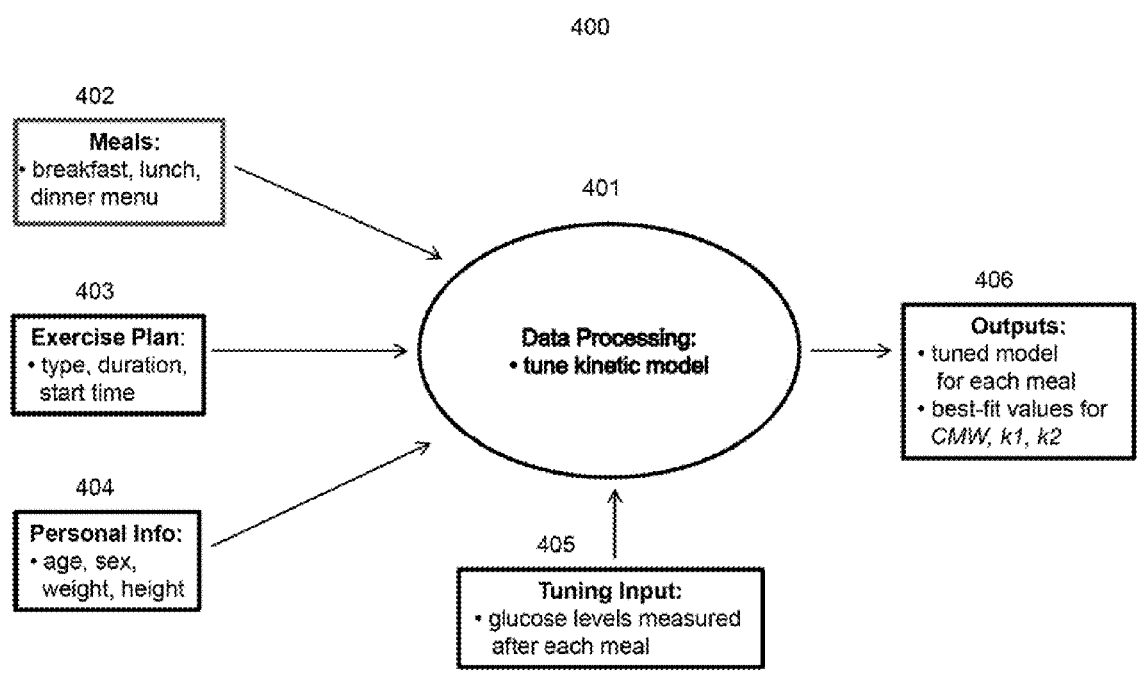
FIG. 4 is a flow diagram of tuning the kinetic model of the method of the invention with an experimentally determined person-specific glucose profile.

FIG. 4 illustrates in details how the kinetic model is tuned in 400. The inputs to the model are: meals comprising breakfast, lunch and dinner menus as shown in 402; exercise plan comprising exercise type, duration and start time of exercise as shown in 403; personal information comprising age, sex, weight and height, as shown in 404; and the blood glucose level data measured after each meal, as shown in 405. The data processing or computation section 401 involves using equation 2 to generate model predicted glucose concentrations with some initial guesses of parameters: CMW, k1 and k2 and then varying the parameter values until the sum of squares of the differences between measured and model-predicted glucose levels is minimized. The outputs from the tuning are the tuned kinetic model with the best-fit values of the parameters: CMW, k1 and k2.

Figure 5:
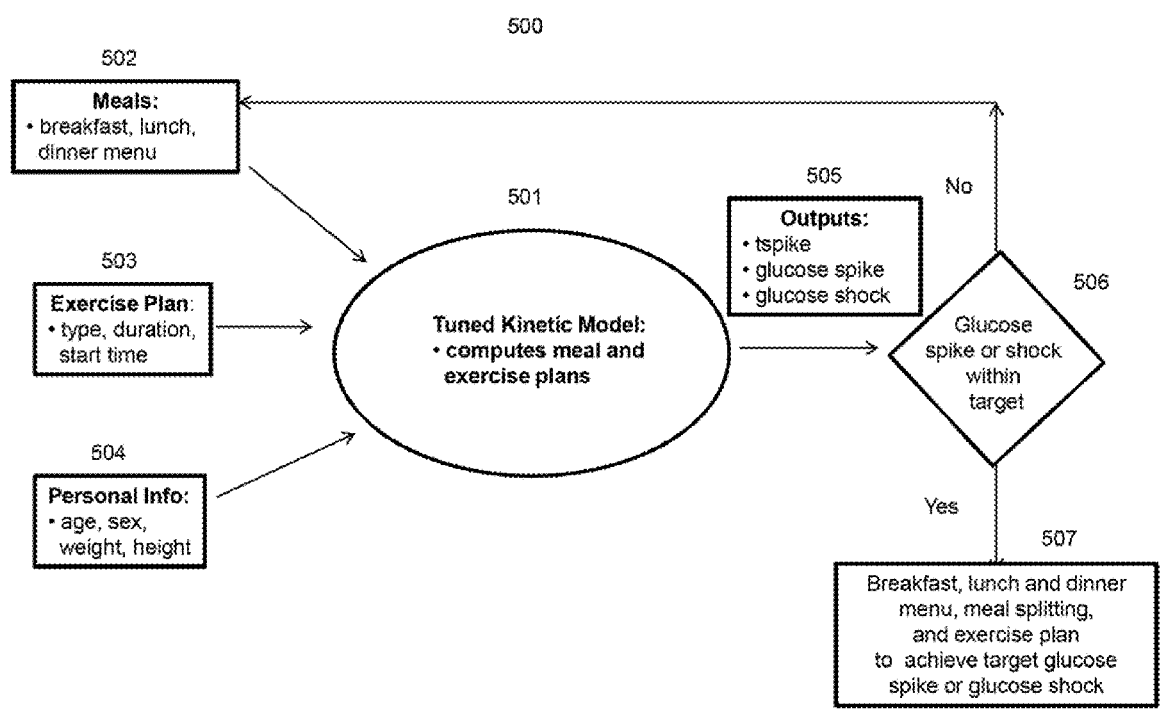
FIG. 5 is a flow diagram of using the tuned kinetic model of the method of the invention to recommend a person-specific meal plan and an exercise plan.

FIG. 5 illustrates in details how the tuned kinetic model is used to develop a meal plan and an exercise plan in 500. The inputs to the model are: meals comprising breakfast, lunch and dinner menus as shown in 502; exercise plan comprising exercise type, duration and start time of exercise as shown in 503; and personal information comprising age, sex, weight and height, as shown in 504. The inputs 502 to the tuned model 501 are initial choices of food and their carbohydrate contents. From these inputs, the total carbohydrate content (Co) for the meal is calculated. These foods should be similar to those used in tuning the model, as discussed earlier using FIG. 4. The tuned kinetic model in processing section 501 then calculates tspike, or glucose spike or glucose shock, which are the outputs 505 of the model. To calculate the glucose shock, the area under the curve of kinetic-model-generated glucose concentrations vs. time is calculated in the post-meal perturbation period, from which the area corresponding to the pre-meal glucose concentration vs. time over the same period is subtracted. If the glucose spike or the glucose shock is higher than the target range in 506, a meal splitting option and/or an exercise plan is selected, and the glucose spike and the glucose shock are calculated again. This process goes through several iterations until the menu for each meal, including meal splitting, and the exercise plan is established for achieving the target glucose spike or glucose shock in 507. In establishing the meal and the exercise plans, the glucose spike should be no more than 2 to 5 mmol/L above the pre-meal glucose level, and the glucose shock should be at least 20% lower than that before following the method of this invention.

Figure 6:
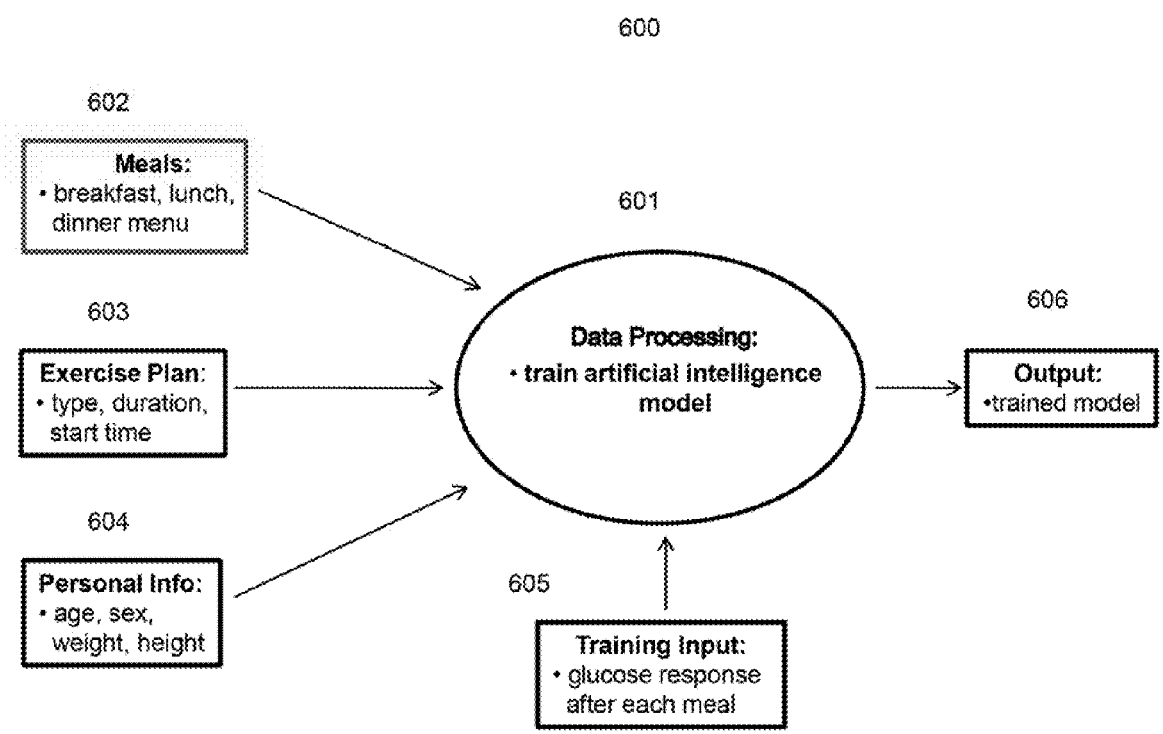
FIG. 6 is a flow diagram of training the artificial intelligence model of the method of the invention with an experimentally determined person-specific glucose profile.

FIG. 6 illustrates how the artificial intelligence model is trained in 600. The inputs to the model are: meals comprising breakfast, lunch and dinner menus as shown in 602; exercise plan comprising exercise type, duration and start time of exercise as shown in 603; personal information comprising age, sex, weight and height, as shown in 604; and the blood glucose level data measured after each meal, as shown in 605. The data processing or computation section 601 involves using an artificial intelligence search algorithm to minimize the cost function until a good match between the model blood glucose predictions and the measured blood glucose values is obtained. The output 606 from the training process is a trained model capable of recommending a meal plan and an exercise plan to lower the glucose spike or the glucose shock to a target range.

Figure 7:
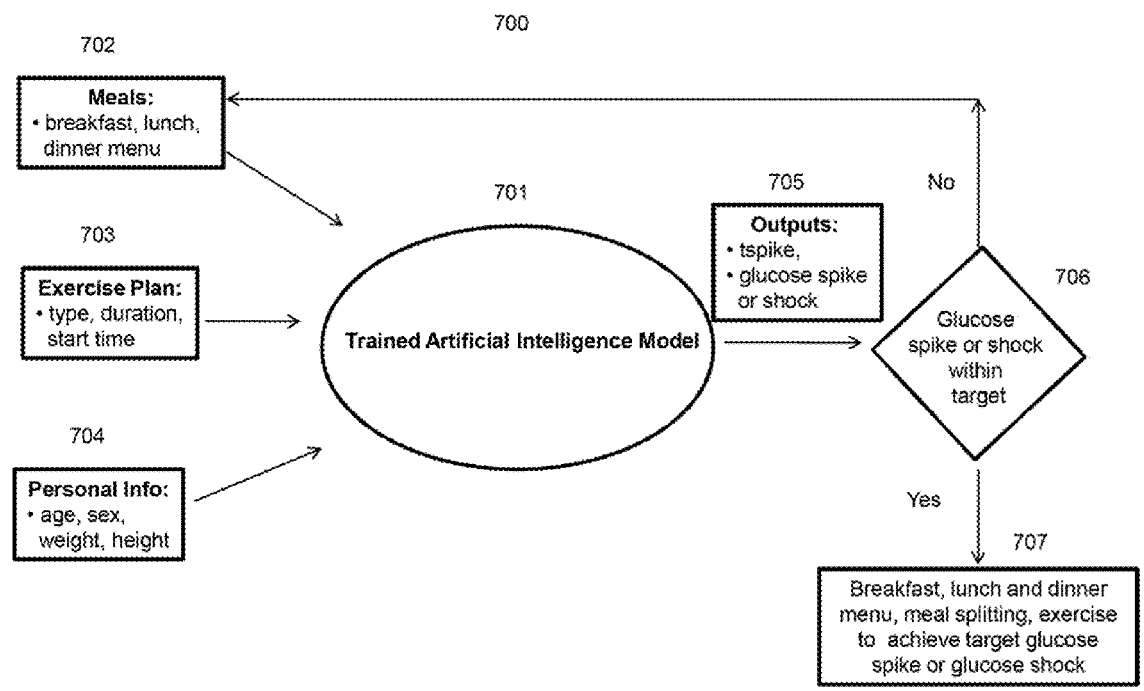
FIG. 7 is a flow diagram of using the trained artificial intelligence model of the method of the invention to recommend a person-specific meal plan and an exercise plan.

FIG. 7 illustrates how the trained artificial intelligence (AI) model 701 is used to develop a meal plan and an exercise plan in 700. The inputs to the model are: meals comprising breakfast, lunch and dinner menus as shown in 702; exercise plan comprising exercise type, duration and start time of exercise as shown in 703; and personal information comprising age, sex, weight and height, as shown in 704. The inputs 702 to the trained model 701 are initial choices of food and their carbohydrate contents, from which the total carbohydrate content (Co) for the meal is calculated. These foods should be similar to those used in training the model, as discussed earlier using FIG. 6. The trained AI model in processing section 701 then calculates tspike, glucose spike or glucose shock, each of which is an output 705 of the model. To calculate the glucose shock, the area under the curve of AI-model-generated glucose concentrations vs. time is calculated in the post-meal perturbation period, from which the area corresponding to the pre-meal glucose concentration vs. time over the same period is subtracted. If the glucose spike or the glucose shock is higher than the target range in 706, a meal splitting option and/or an exercise plan is selected, and the glucose spike and the glucose shock are calculated again. This process goes through several iterations until the menu for each meal, including meal splitting, and the exercise plan is established for achieving the target glucose spike or glucose shock in 707. In establishing the meal and the exercise plans, the glucose spike should be no more than 2 to 5 mmol/L above the pre-meal glucose level, and the glucose shock should be at least 20% lower than that before following the method of this invention.

Figure 8:
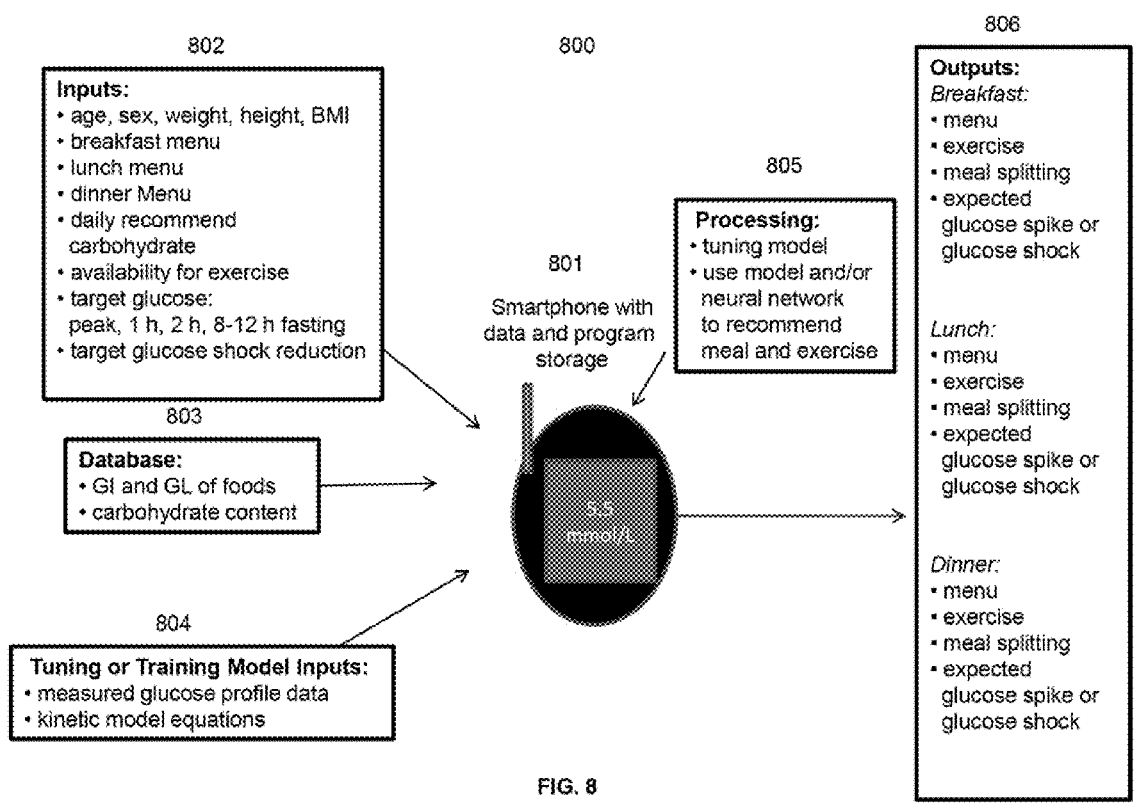
FIG. 8 is a block diagram showing the embedding of the method of the invention in a Smartphone with computation and display capabilities.

FIG. 8 illustrates how the method 200 can be implemented using a Smartphone environment 800. The Smartphone 801 can be any mobile phone with computation capability and access to Internet. It may have disk storage devices (hardware). Software with a set of instructions is developed and embedded in the Smartphone. The software and the hardware work together to tune or train the blood glucose model. The tuned or the trained model is used to recommend a meal and a post-prandial exercise plan for each significant meal.

The inputs 802 may include, but not limited to, personal information (age, sex, weight, height, body frame size, BMI), which may be used to calculate the blood volume and the daily recommended carbohydrate need and protein need of the person for whom the plan is being developed. The inputs may also include a preferred breakfast menu, a lunch menu and a dinner menu for the individual. The inputs also include if time is available for exercise for a given day and after a given meal. Inputs also include the target blood glucose levels at tspike and at different times.

In practicing the invention, the Smartphone environment 800 may also advantageously use existing databases 803 from the literature and store them in the computer. These databases include, but not limited to, data on carbohydrate content, GI and GL of different food items. Additional input includes the target glucose shock reduction.

The Smartphone environment 800 may also need data for tuning or training the blood glucose model, as shown in box 804 in FIG. 8. These may comprise measured glucose profile data of an individual after each significant meal. The significant meal may include breakfast, lunch and dinner. Having one profile for each meal may be advantageous as the food intake and metabolism may vary from morning to afternoon to evening. In addition to the personal glucose profile data for each meal, the Smartphone environment 800 also needs the kinetic model equations (equations 2, 3, and 4) to recommend a meal plan and an exercise plan.

Box 805 is the processing section of the method in the Smartphone environment 800, where the tuning and/or training of the model as well as computation takes place to recommend a meal plan and an exercise plan to achieve a target glucose concentration.

Box 806 is the output section of the method in the Smartphone environment 800. The outputs of box 806 are stored in memory for display or plotting. The outputs may include suggested breakfast, lunch and dinner menu for a day in order to keep the glucose spike or glucose shock for each meal to a target range. The outputs may also include the level of exercise needed for the day given the meal menu. The outputs may also include the historical measured glucose concentration in a tabular format or as a plot.

Figure 9:
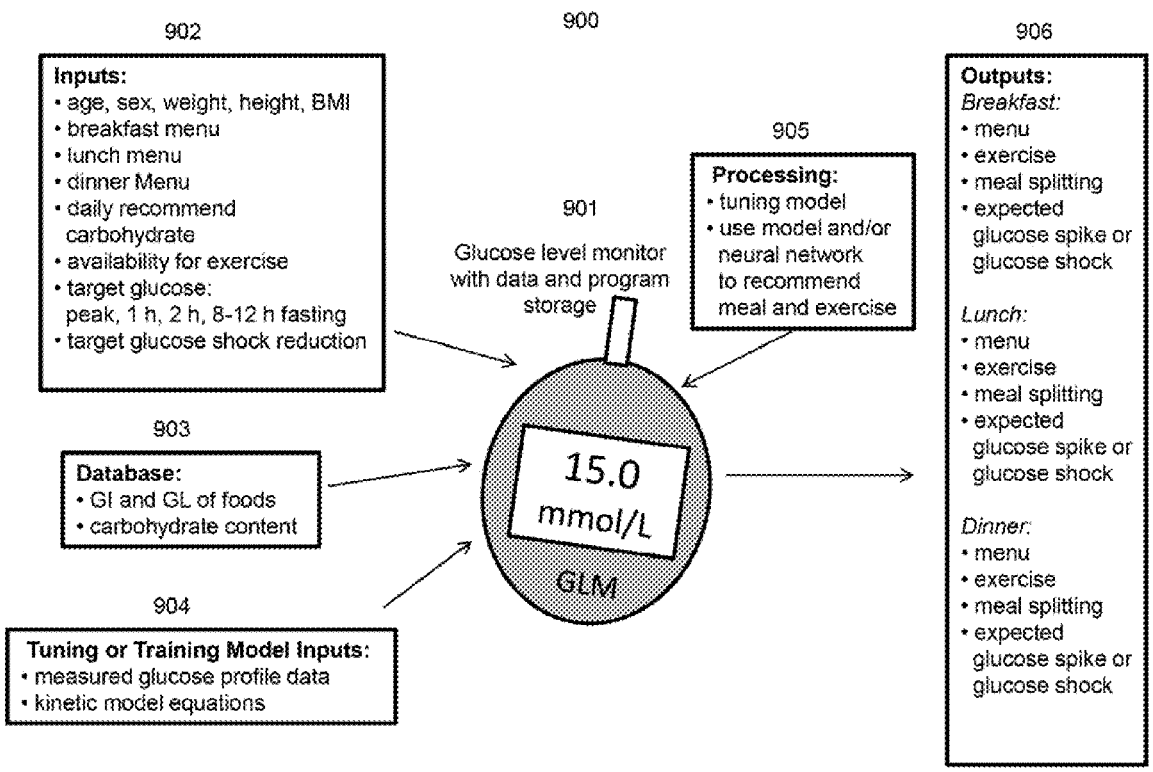
FIG. 9 is a block diagram showing the embedding of the method of the invention in a glucose level monitor with computation and display capabilities.

FIG. 9 illustrates how the method 200 can be implemented using a glucose monitoring device 900. The glucose monitoring device 901 can be any glucose monitoring device with computation capability and access to Internet. It may have disk storage devices (hardware). Software with a set of instructions is developed and embedded in the glucose monitoring device. The software and the hardware work together to tune or train the blood glucose model. The tuned or the trained model is used to recommend a meal and a post-prandial exercise plan for each significant meal.

The inputs 902 may include, but not limited to, personal information (age, sex, weight, height, body frame size, BMI), which may be used to calculate the blood volume and the daily recommended carbohydrate need and protein need of the person for whom the plan is being developed. The inputs may also include a preferred breakfast menu, a lunch menu or a dinner menu for the individual. The inputs also include if time is available for exercise for a given day and given meal. Inputs also include the target blood glucose levels at tspike, and at different times. Additional input includes the target glucose shock reduction.

In practicing the invention, the glucose monitoring option 900 may also advantageously use existing databases 903 from the literature and store them glucose monitoring device. These databases include, but not limited to, data on carbohydrate content, GI and GL of different food items.

The glucose monitoring device 900 may also need inputs for tuning or training the blood glucose model, as shown in box 904 in FIG. 9. These include measured glucose profile data of an individual after each significant meal. The significant meal may include breakfast, lunch and dinner. Having one profile for each meal may be advantageous as the food intake and metabolism may vary from morning to afternoon to evening. In addition to the personal glucose profile data for each meal, the glucose monitoring device 900 also needs the kinetic model equations (equations 2, 3, and 4) as inputs.

Box 905 is the processing section of the method using the glucose monitoring option 900, where the tuning and/or training of the model as well as computation takes place to recommend a meal plan and an exercise plan to achieve a target glucose concentration.

Box 906 is the output section of the method in the glucose monitoring option 900. The outputs of box 906 are stored in memory for display or plotting. The outputs may include suggested breakfast, lunch and dinner menu for a day in order to keep the glucose spike or glucose shock for each meal to a target range. The outputs may also include the level of exercise needed for the day for the suggested meal menu. The outputs may also include the historical measured glucose concentration in a tabular format or as a plot.

In implementing the method, one of ordinary skill may refer to:

1. the flow diagram in FIG. 2 and its description earlier in the disclosure for controlling the glucose spike or the glucose shock according to one embodiment of the invention;
2. the block diagram in FIG. 3 and its description earlier in the disclosure for embedding the method in a computer;
3. the flow diagram in FIG. 4 and its description earlier in the disclosure for tuning the kinetic model of the method with an experimentally determined glucose profile for a person for each significant meal: breakfast, lunch or dinner;
4. the flow diagram in FIG. 5 and its description earlier in the disclosure for using the tuned kinetic model of the method to recommend a person-specific meal and an exercise plan;
5. the flow diagram in FIG. 6 and its description earlier in the disclosure for training the artificial intelligence model of the method with an experimentally determined glucose profile for a person for each significant meal: breakfast, lunch or dinner;
6. the flow diagram in FIG. 7 and its description earlier in the disclosure for using the trained artificial intelligence model of the method to recommend a person-specific meal and an exercise plan;
7. the flow diagram in FIG. 8 and its description earlier in the disclosure for embedding the method of this invention in a Smartphone with computation capability;
8. the flow diagram in FIG. 9 and its description earlier in the disclosure for embedding the method of this invention in a glucose monitoring device with computation capability.

The embodiments of the invention and its advantages over prior art in developing an individualized, quantitative plan for managing Type 2 diabetes, reducing body weight and abdominal fat are further illustrated by the following examples. While these examples may enable one of ordinary skill in the art to practice the embodiments of the invention, there are other variations possible without deviating from the scope and the spirit of the invention.

EXAMPLES

Example 1

Reducing Abdominal Fat and Body Weight by Following the Method of this Invention A runner carried abdominal fat that was conspicuous even after completing 13 consecutive marathons over 10 years. After reducing the post-prandial glucose spike and the glucose shock by following the meal splitting and the post-meal exercise plans recommended by the tuned person-specific blood glucose response model of the instant invention, he was able to get rid of the abdominal fat, while losing 6 kg of body weight from an initial weight of 70 kg in six weeks.

Both abdominal fat and body weight reductions were achieved without lowering total carbohydrates intake and without taking any medicine.

This example shows that the person-specific, quantitative method of this invention is superior to strenuous training required for completing multiple marathons in terms of losing abdominal fat and body weight.

Example 2

Lowering Blood Glucose Level from Diabetic to Normal Range by Practicing this Invention (Comparative Example)

After completing 13 consecutive marathons over 10 years, the runner from Example 1, was diagnosed with Type 2 diabetes with a 12-hour fasting glucose level of 7.7 mmol/L and symptoms of shortness of breath, numbness in toes, fingers and around the skull. This diagnosis was unexpected in view of his healthy life style, diet and fitness level.

Figure 10:
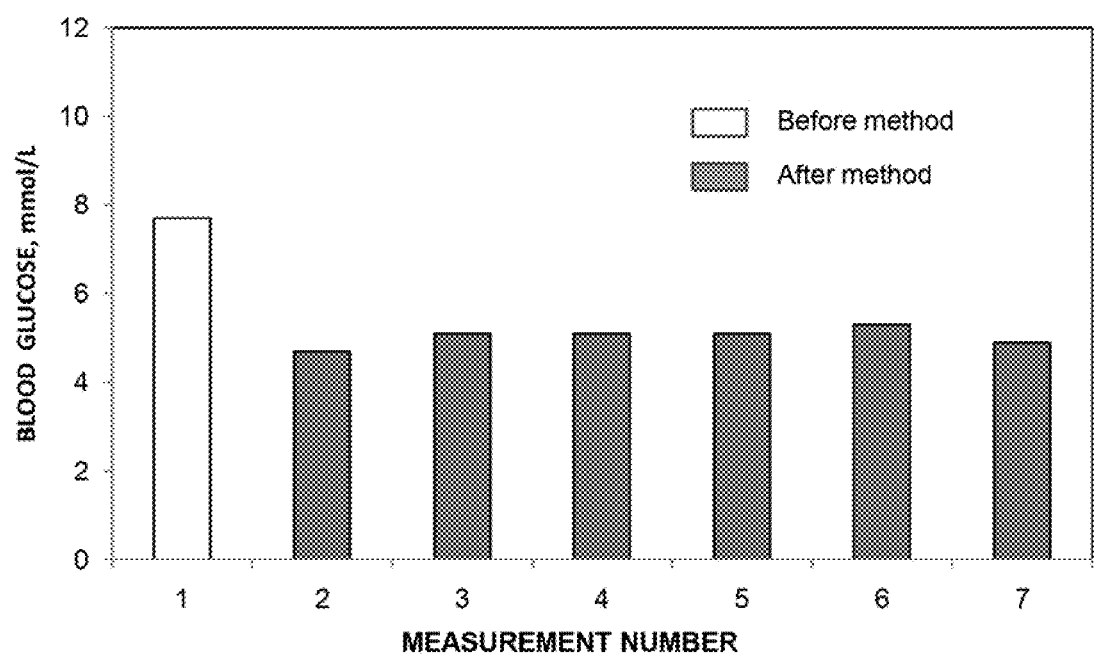
FIG. 10 is a comparison of the 12-hour fasting blood glucose level of a Type 2 diabetes patient before and after following the method of this invention.
Figure 11:
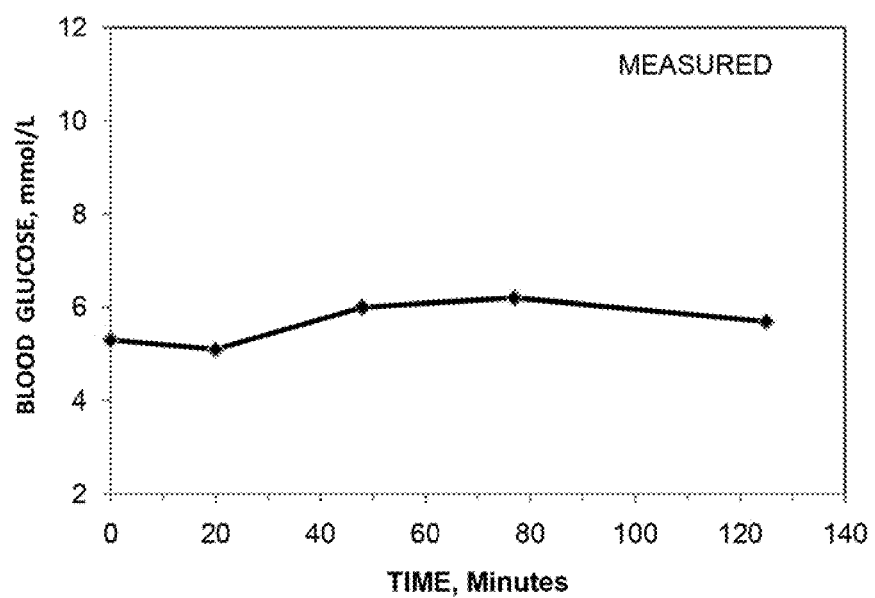
FIG. 11 is a stabilized post-prandial blood glucose level achieved following the method of this invention.

Within six weeks of following the method of this invention, the runner was able to lower his 12-hour fasting glucose level from the diabetic to a normal range. The first non-shaded column in FIG. 10 shows the 12-hour fasting glucose before using the method of this invention to be 7.7 mmol/L, which is in the diabetic range. The same figure also shows in darker shaded columns the 12-hour fasting glucose levels over six consecutive days after the runner had used the method of this invention. The glucose levels varied over a narrow range of 4.7 to 5.3 mmol/L, with an average of 5.0 mmol/L and a small standard deviation of 0.21 mmol/L. The numbness in parts of the body experienced before practicing the method slowly disappeared along with the shortness of breath, enabling the runner to complete a half-marathon at a time close to his personal best time. The glucose uptake from blood to muscles also improved as confirmed by the relatively flat after-dinner glucose profile (FIG. 11). An oral glucose tolerance test by taking 75 g of glucose solution showed that the 2-hour glucose level was normal, confirming the absence of Type 2 diabetes. No medication was used in correcting the Type 2 diabetes.

This turnaround resulted from eating each significant meal as recommended by the personalized tuned model of this invention, occasional meal splitting, and doing moderate physical activity within two hours of a significant meal—all aimed at lowering the post-prandial glucose spike or the glucose shock.

This example shows that the qualitative guidelines in the prior art are not effective even for an active marathon runner in lowering the blood glucose level. The prior guidelines lacked specificity as to the timing of physical activity and more importantly, did not emphasize the need for controlling the post-prandial glucose spike. By sharp contrast, the individualized, quantitative method of this invention was effective not only in lowering the 12-hour fasting glucose level, but also in correcting Type 2 diabetes.

Example 3

Generating a Personal Blood Glucose Profile, According to this Invention

In generating a personal, meal-specific glucose profile for the runner from Examples 1 and 2, an experimental program was designed, and the experimental data collected and recorded in a spreadsheet embedded in a desktop computer with an XP Professional operating system and a Samsung monitor. The blood glucose level was monitored using an OneTouch UltraSmart monitor, OneTouch Ultra Test Strips and OneTouch UltraSoft lancets, manufactured by LifeScan Inc. Milpitas, Calif., USA. The monitor was checked for accuracy using the OneTouch Ultra control solution. The pre-breakfast glucose level and the glucose levels after breakfast were monitored at different times to identify the tspike and the Gmax. Movement of body parts was minimized during the test period so as not to introduce any confounding effect of physical activity on the results. The measurements were continued until the blood glucose level stabilized, approaching the pre-meal glucose level.

Figure 12:
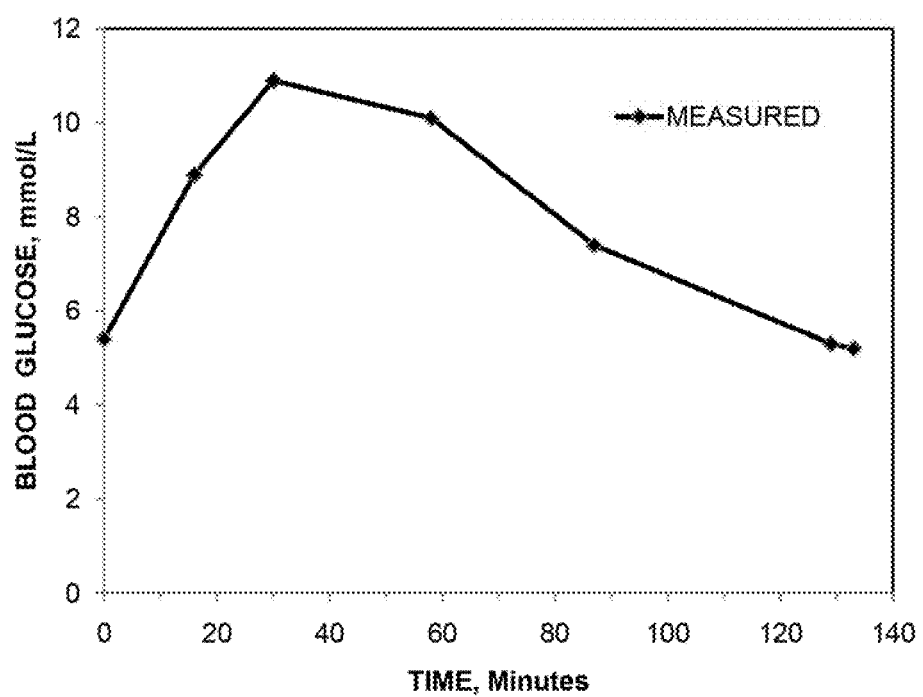
FIG. 12 is a measured personal post-breakfast blood glucose profile generated following the method of this invention.

The runner had a pre-meal blood glucose concentration—measured at a finger tip—of 4.9 mmol/L after 10 hours of overnight fasting. It should be noted that at the time of this test the runner had already been practicing the teachings of the instant invention and was able to reduce his 10-hour fasting glucose from 7.7 mmol/L to an average of 5.0 mmol/L, as discussed in Example 2. After measuring his pre-meal blood glucose level, the runner had a breakfast consisting of a half cup of high-fiber cereal (Fiber 1, whole grain by General Mills), ½ cup Lucerne fat-free skimmed milk and a half cup of fresh blue berries, with a net carbohydrates (subtracting for the fibers) intake of 23.7 g. After eating the breakfast at time t=0, the blood glucose levels at the finger tips were measured at t=16, 30, 58, 87, 129 and 133 minutes, without performing any physical activity from the start to the end of the test period. The glucose levels measured at different times are shown in FIG. 12—in solid diamond markers joined by a solid curve—as a post-prandial blood glucose profile. The glucose reached a maximum concentration of 10.9 mmol/L at 30 minutes following the meal, creating a glucose spike of 6.0 mmol/L, relative to the pre-meal glucose level. The glucose concentration then dropped to 5.2 mmol/L—close to the pre-meal glucose level of 4.9 mmol/L—at 133 minutes.

This example shows that even a relatively light breakfast with a high fiber cereal may create a significant glucose spike in a marathon-fit person. It also highlights the drawback of measuring the blood glucose level at two hours after a meal—in accordance with the recommendations in the prior art—which would have missed the glucose spike occurring at 30 minutes after the meal. Uncontrolled glucose spikes over time may transform a person with a normal glucose level to a pre-diabetic, and a pre-diabetic person to a Type 2 diabetic, increasing the risk of cardiovascular, retinal and renal diseases.

Example 4

Figure 13:
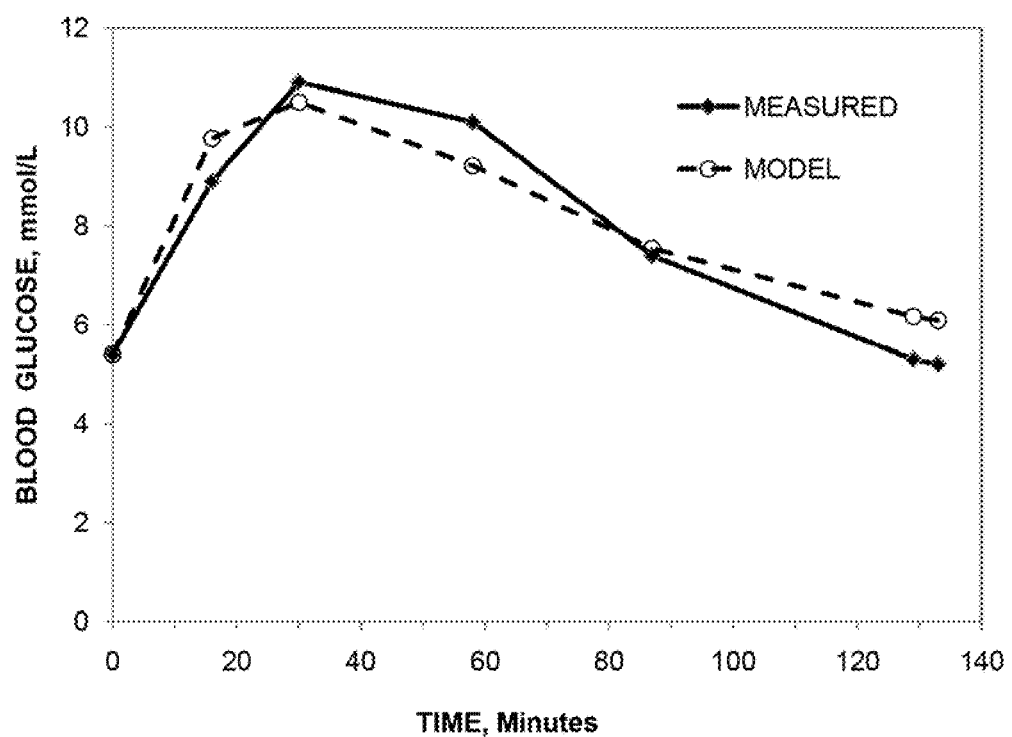
FIG. 13 is a comparison of the measured post-breakfast blood glucose levels with those computed by the person-specific tuned blood glucose response model.

Tuning the Blood Glucose Kinetic Model with Post-Prandial Glucose Profile Data, According to this Invention The post-prandial blood glucose profile data of the runner from Example 3 was used to tune the blood glucose kinetic model (equation 2), according to this invention, using non-linear regression based on minimization of the sum of squares of the differences between measured and model-predicted blood glucose concentrations. The tuning was done in the computing environment of Example 3 in a spreadsheet by treating CMW, k1 and k2 as adjustable or tunable parameters. The best-fit value for CMW, the molecular weight of the complex carbohydrates ingested in Example 3, was 285 g/mole, compared to a molecular weight of 180.2 g/mole for glucose. The model-generated glucose profile for the runner is shown in FIG. 13 as a dashed curve. Superimposed on this figure is the measured glucose profile from Example 3 as a solid curve. The agreement between the model predictions and the measured values is good. The tspike, according to the tuned model, calculated using equation 3 and the best-fit values of the three parameters (CMW, k1 and k2), is 29.5 minutes, which is also in agreement with the measured tspike of 30 minutes. The model-predicted Gmax is 10.5 mmol/L compared to the experimental value of 10.8 mmol/L. One of ordinary skill should recognize that the glucose profile in this example is not only person-specific, but also meal-specific (for breakfast) and food-specific (for the foods listed in Example 3).

This example illustrates a significant advantage of the invention over prior art by allowing the development of a tuned individualized, meal-specific, quantitative model which can be used for recommending a personalized meal plan and an exercise plan to control post-prandial glucose spike.

Example 5

Use of Tuned Individualized Model to Show the Effect of Meal Splitting on Glucose Spike or Glucose Shock, According to this Invention The tuned model from Example 4 was used to show the effect of splitting the breakfast meal by half and taking one-half of the meal in one sitting. For this calculation, the carbohydrates intake by the runner in Example 3 was reduced by half, and the tuned runner-specific kinetic model from Example 4 was used to calculate the blood glucose levels at predetermined times. The blood glucose profile with the split meal is shown as a dotted curve in FIG. 14 in which the full meal measured glucose profile, shown as a solid curve, and the model-predicted blood glucose profile for the full meal, shown as a dashed curve, are also included for comparison.

Figure 14:
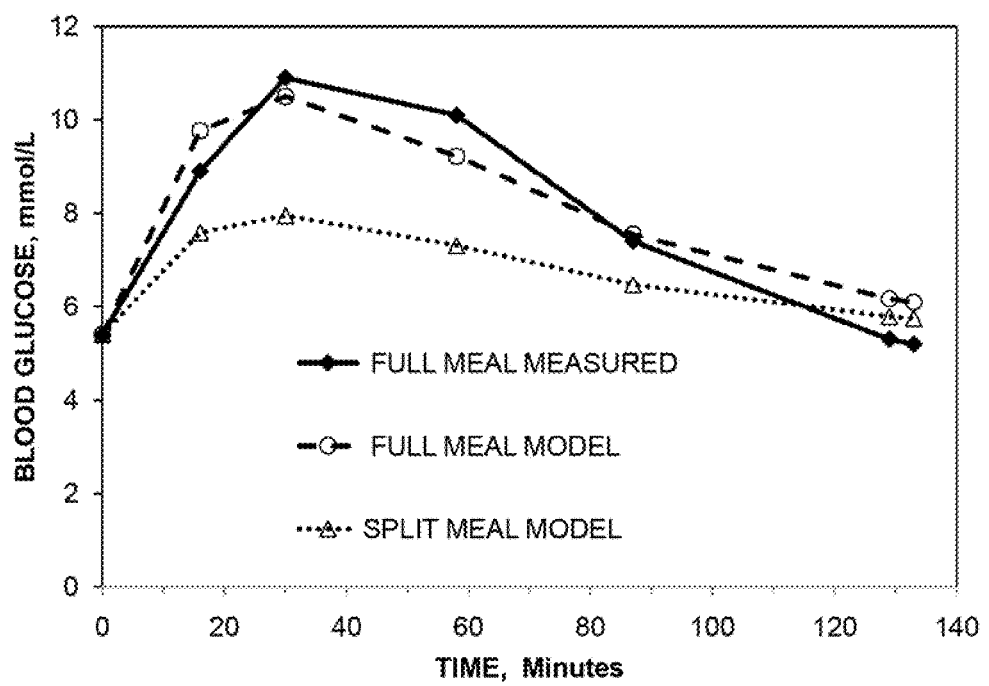
FIG. 14 is a comparison of the model-computed post-breakfast blood glucose levels after the meal has been taken by splitting it by half with those computed by the tuned model for a full meal (dashed curve), and those measured after taking a full meal (solid curve).

As shown in FIG. 14, by splitting the breakfast meal by half, the maximum glucose level is reduced from 10.9 mmol/L to 8.0 mmol/L. The area under the glucose concentration vs. time plot—in the post-meal perturbation period—with the split meal case is reduced by 50% (after correcting for the base area corresponding to the pre-meal glucose concentration) compared to that with the full meal case, indicating a glucose shock reduction of 50%. FIG. 14 also suggests that by taking the second half of the split breakfast after 90 minutes of taking the first split meal may keep the second maximum glucose level close to 8.0 mmol/L. Thus using the tuned model of this invention, the effect of meal splitting on glucose spike or glucose shock reduction can be quantified and a meal plan can be recommended to lower the risks of developing various glucose-spike-induced diseases, or, help manage those diseases more effectively, if already developed.

Example 6

Figure 15:
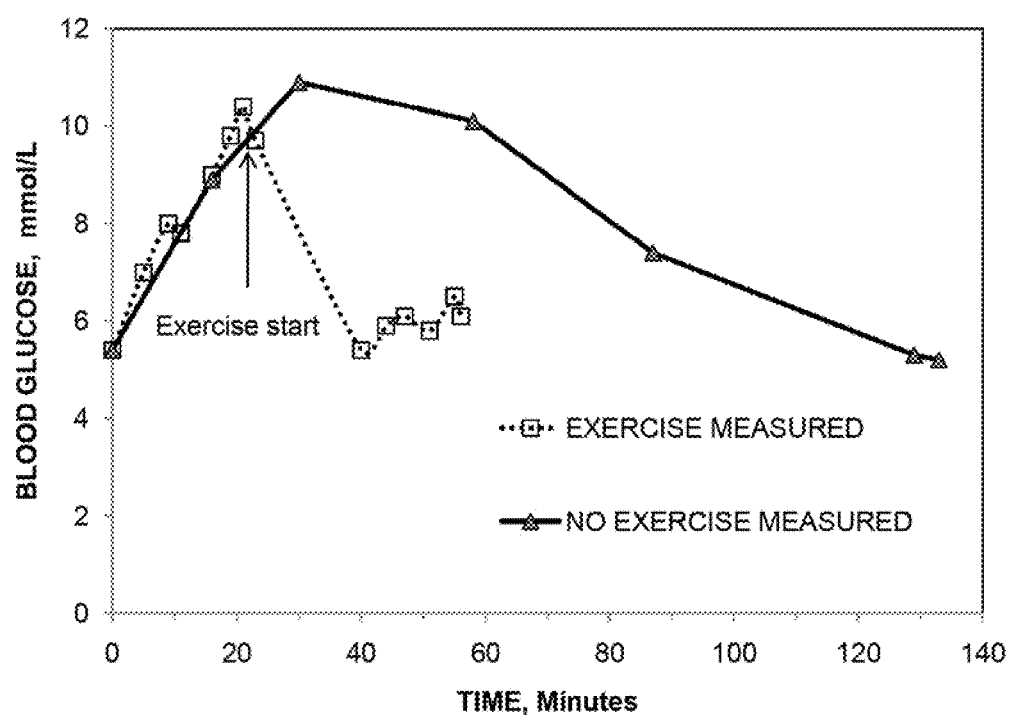
FIG. 15 is a comparison of the measured post-breakfast blood glucose levels after performing post-prandial exercise with those measured after taking a full meal breakfast but without performing any exercise.

Reducing Blood Glucose Spike by Performing Post-Prandial Exercise According to this Invention The runner from Examples 1, 2, and 3 had a pre-meal blood glucose concentration of 5.1 mmol/L. The net carbohydrates (subtracting for fibers) intake during a breakfast was 23.7 g. The glucose level rose to 10.4 mmol/L after 31 minutes of having the breakfast, at which time the runner went for a run at a moderate pace of 7.5 min per km. The measured blood glucose profile with exercise is shown as a dotted curve and the measured glucose profile without exercise as a dashed curve in FIG. 15. At the end of the 12-minutes run, the glucose level fell to 5.4 mmol/L, which is very close to the pre-meal glucose level (FIG. 15). The time to achieve this low glucose level was three times faster than the time of 133 minutes needed to achieve the same glucose level without performing any exercise, as shown in FIG. 15. This results in a 68% reduction in the post-meal perturbation period and a 70% reduction of the area under the glucose concentration vs. time curve (after correcting for the base area corresponding to the pre-meal glucose concentration) over the case without exercise. As a result, the runner's vital organs and systems are exposed to a glucose shock that was 70% lower than that without the post-prandial exercise. FIG. 15 also suggests that starting exercise sooner than 31 minutes may reduce the glucose spike or the glucose shock even more.

This example shows the benefit of post-meal exercise to lower the post-prandial blood glucose level and the associated health risks. Had the runner waited two hours or longer before commencing the exercise, following the prior art guidelines, the opportunity for reducing the high glucose level exposure would have been missed.

Example 7

Figure 16:
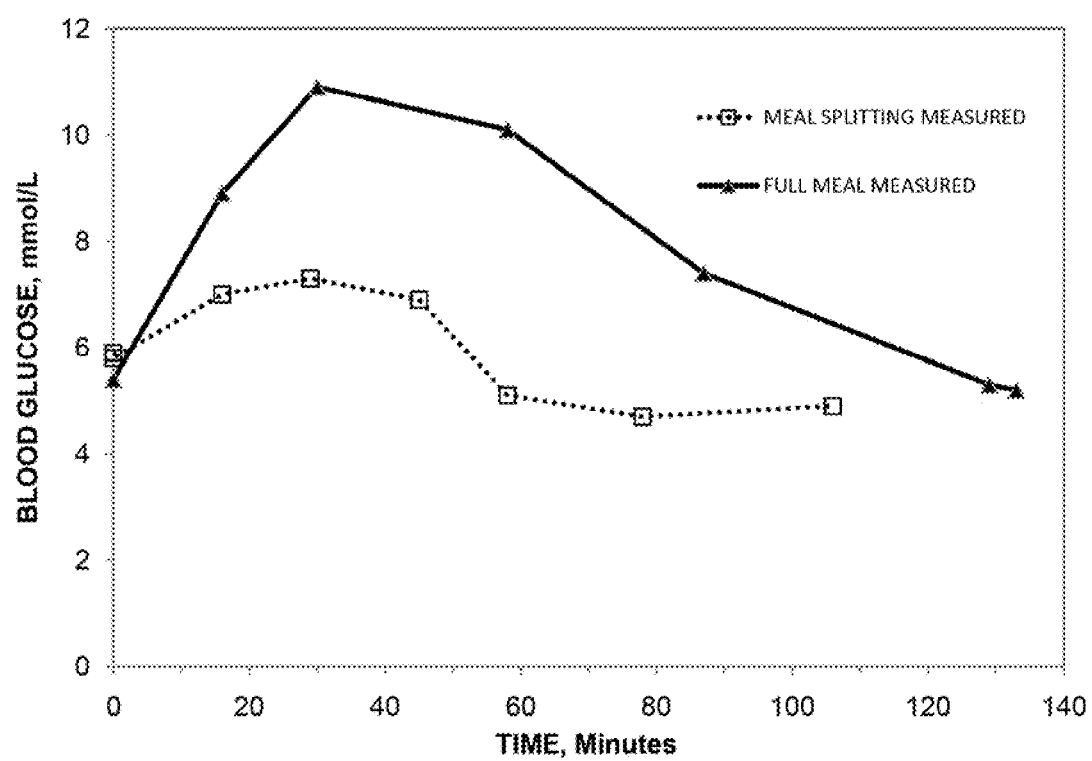
FIG. 16 is a comparison of the measured post-breakfast blood glucose levels after the meal has been taken by splitting it by half with those measured after a full meal breakfast.

Reducing Glucose Spike by Meal Splitting (Actual Test), According to this Invention The runner from Examples 1, 2, 3, and 6 had a pre-meal blood glucose concentration of 5.8 mmol/L. On that day, he could not do any post-meal exercise because of prior commitment. To reduce the maximum glucose level of 10.9 mmol/L from Example 3, the runner split the meal from Example 3 into two equal halves and took the first half in one sitting. As shown in FIG. 16, through meal splitting, the post-prandial glucose maximum was lowered to 7.1 mmol/L from 10.9 mmol/L in Example 3. The glucose level dropped to 5 mmol/L within an hour of taking the meal. The area under the glucose concentration vs. time plot in the post-meal perturbation period was also reduced by 80% (after correcting for the base area corresponding to the pre-meal glucose concentration) over the case with a full meal, indicating a 80% reduction in the glucose shock to the vital organs and systems. The runner then took the other half of the split breakfast an hour later which led to a glucose maximum of only 7.1 mmol/L (not shown in FIG. 16)—which was only 1.3 mmol/L higher than the pre-meal level. The reductions of the glucose spike and the glucose shock were accomplished by splitting the meal in two portions and taking the portions one hour apart without reducing the total food intake.

This example along with Example 5 shows the benefit of semi-continuous feeding of this invention in reducing blood glucose spike or glucose shock.

Example 8

Assuaging the Symptoms of Aging, According to this Invention

The 60 year old runner from Examples 1, 2, 3, 6 and 7, was experiencing reduced ability to think, cognitive decline and a lack of energy while running—all symptoms of aging. After controlling the post-prandial glucose spike or glucose shock, according to this invention, his ability to think through complex scientific problems improved as he made several scientific inventions, and his energy level during running improved as he qualified for the Boston Marathon after fourteen attempts.

Example 9

Figure 17:
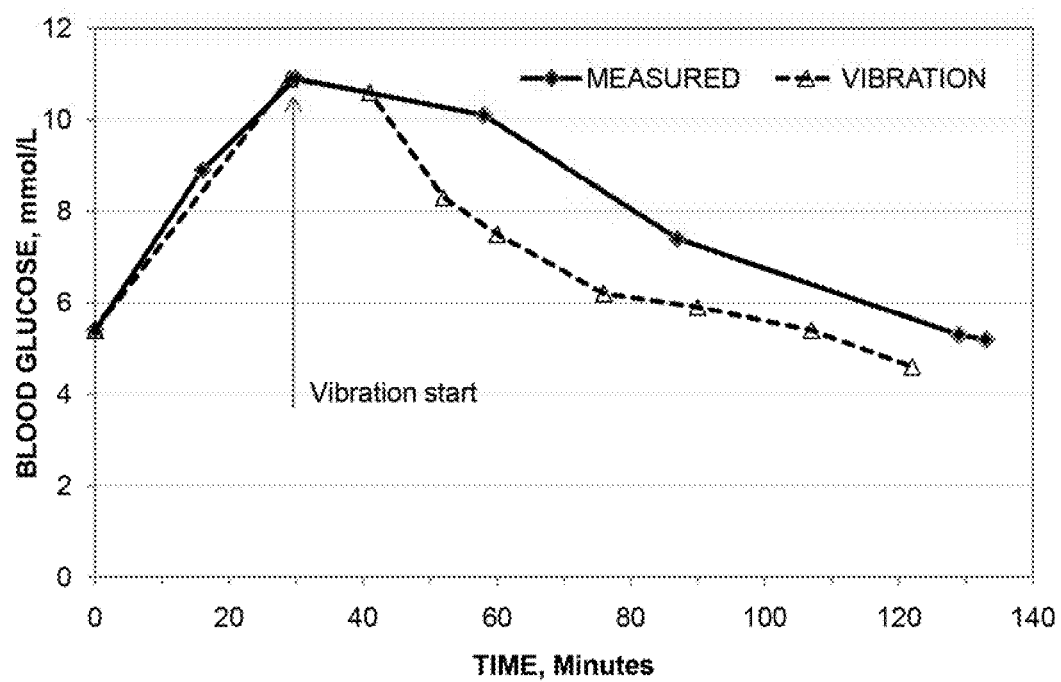
FIG. 17 is a comparison of the measured post-breakfast blood glucose levels after using a machine for post-prandial leg vibration while sitting in a chair with those measured after a full meal breakfast.
Figure 18:
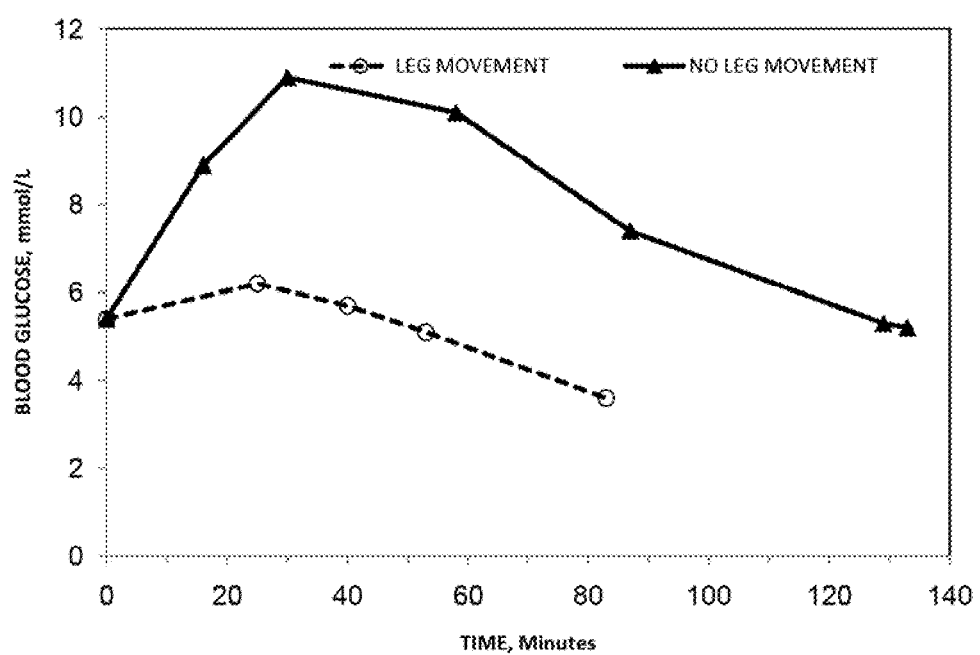
FIG. 18 is a comparison of the measured post-breakfast blood glucose levels after using a specially designed foot exerciser for post-prandial leg movement with those measured after a full meal breakfast.

Reducing Blood Glucose Shock Using Post-Prandial Feet Vibration, According to this Invention The runner from Examples 1, 2, 3, 6, 7 and 8 had a breakfast consisting of a half cup of high-fiber cereal (Fiber 1, whole grain by General Mills), ½ cup Lucerne fat-free skimmed milk and a half cup of fresh blue berries, with a net carbohydrates (subtracting for the fibers) intake of 23.7 g. His blood glucose level rose from pre-breakfast level of 5.4 mmol/L to 10.9 mmol/L, 29 minutes after the breakfast. Thirty minutes after eating the breakfast the runner placed his feet—sitting on a chair—on a Masaaki Foot Massager vibration machine set at the lowest vibration speed setting of 1 (the machine speed scaler 1 to 15), and continued monitoring the blood glucose levels at different times for 32 minutes during vibration. As shown in FIG. 17, the glucose shock, measured by the area under the glucose concentration vs. time curve, after subtracting the area corresponding to the pre-meal glucose concentration, was reduced by 33% using the low-speed feet vibration.

This example shows that post-prandial glucose shock can be reduced conveniently using leg vibration, while sitting on a chair at home watching TV or using a computer, or at office doing work sitting by a desk.

Example 10

Reducing Blood Glucose Shock Using Post-Prandial Leg Movement, According to this Invention The runner from Examples 1, 2, 3, 6, 7, 8 and 9, with a pre-breakfast glucose level of 5.4 mmol/L, ate a breakfast consisting of a half cup of high-fiber cereal (Fiber 1, whole grain by General Mills), ½ cup Lucerne fat-free skimmed milk and a half cup of fresh blue berries, with a net carbohydrates (subtracting for the fibers) intake of 23.7 g. Right after eating the breakfast, the runner started moving his legs up and down—sitting on a chair while using a home computer—by pressing his feet up and down on the movable foot rest of a leg exerciser. As shown in FIG. 17, the post-prandial glucose spike was reduced by 43% and the glucose shock was reduced by 9.0% by performing the post-meal leg movement while sitting on a chair.

This example shows that post-prandial glucose shock can be reduced using leg movement, while sitting at home watching TV or using a computer, or at office while doing work sitting by a desk.

Example 11

Reducing Hair Loss, According to this Invention

The runner from Examples 1, 2, 3; 6, 7, 8, 9 and 10, with a head full of hair started losing hair severely after being diagnosed with high blood glucose and Type 2 diabetes. After controlling the glucose spike, or the glucose shock following the method of this invention, he was able to prevent any further hair loss.

This example shows the effectiveness of the method of this invention in dealing with hair loss.

Quite unexpectedly, all these desirable results described—for example, losing body weight and abdominal fat, correcting Type 2 diabetes, assuaging the symptoms of aging—were achieved by following the teachings of this invention and without taking any medication or reducing the total food intake. Also surprisingly, the timely moderate physical activities performed during the post-prandial perturbation period were superior to the strenuous long-distance running, including completion of multiple marathons, for reducing abdominal fat, body weight, Type 2 diabetes blood glucose level and aging symptoms.

The embodiments and the examples also show how the personalized, quantitative method may help an individual patient, health care providers, nutritionists and dieticians in managing obesity, abdominal fat, pre-diabetes, diabetes, hypoglycemia, aging, the cardiovascular diseases, cancer or other diseases that are induced by the post-prandial glucose spike, or the glucose shock.

We claim:

1. A method for lowering the risk of developing blood-glucose-spike-induced diseases, or for managing the said diseases, if already developed, the method comprising the steps of:
   (a) generating, through measurements, a person-specific profile of glucose concentration vs. time for at least one significant meal, the profile indicating the timing and the amplitude of a glucose spike;
   (b) tuning or training a blood glucose response model with the measured person-specific blood glucose profile data for at least one meal to determine the best-fit values of meal-specific and person-specific parameters in the tuned model, or to obtain a trained blood glucose response model; wherein the blood glucose response model is a kinetic model for the reactions of carbohydrates (C) to glucose (G) to glycogen (GLY) and energy (E): C→G→GLY and E that yields a mathematical expression relating the blood glucose level at any time t since taking a meal with three measurable or known factors, and three tunable parameters, the said kinetic model is as shown by:

$$G = G_o + 1000*((C_o/CMW)/BV)*[k1/(k2-k1)]*[\exp(-k1*t) - \exp(-k2*t)]$$

where, G is the blood glucose concentration at any time following a meal, in mmol/L;
   Go is the blood glucose concentration prior to taking a meal, in mmol/L;
   Co is carbohydrate ingested during a meal, in g;
   BV is the blood volume of the person, in liters;
   CMW is a meal-specific tunable parameter representing the average molecular weight of the carbohydrates ingested during a meal, in g/mol;
   k1 is a person-specific tunable parameter representing the rate constant for the reaction C→G, in min$^{-1}$;
   k2 is a person-specific tunable parameter representing the rate constant for the reaction G→GLY and E, in min$^{-1}$;
   t is the time from the start of the most recent meal, in min;
   wherein the said kinetic model is tuned with the person-specific glucose profile data to determine the best-fit or the tuned values of CMW, k1 and k2, and which values are then used along with pre-meal Go, Co ingested, and BV to calculate:
   (1) G in blood level at any time following a meal using the kinetic model;
   (2) tspike, the time to reach the glucose spike using the best-fit or the tuned values of k1 and k2 from equation 3 below:

$$tspike = [1/(k1-k2)]*\ln(k1/k2);$$

(3) the glucose spike (Gmax) using the best-fit or the tuned values of CMW, k1 and k2, and the known values of Go, Co and BV from equation 4 below:

$$Gmax = G_o + 1000*((C_o/CMW)/BV)*[k1/(k2-k1)]*[\exp(-k1*tspike) - \exp(-k2*tspike)];$$ and (4) the glucose shock following a meal by subtracting the base area (corresponding to the pre-meal) from the area under post-meal G vs. t plot, over the same period; and
   wherein at least one of which calculated values (G, tspike, Gmax or glucose shock) is used to develop a meal plan and/or a post-prandial exercise plan to keep the glucose spike, or the glucose shock following a meal within a target level, thereby lowering the risk of developing blood-glucose-spike-induced diseases, or for managing the said diseases, if already developed.
   (c) using the tuned or the trained blood glucose response model to develop at least one significant meal plan and/or a post-prandial exercise plan, needed for reducing the post-prandial glucose spike, or the glucose shock, defined by the increase in area over the pre-meal area under the blood glucose concentration vs. time plot, to a target level; and
   (d) executing the meal and/or the post-prandial exercise plan and comparing the measured blood glucose spike, or the glucose shock with a target range to assess the success of the glucose spike reduction plan, and readjusting, if necessary, the meal and/or the post-prandial exercise plan using the tuned or the trained blood glucose response model.

2. The method according to claim 1, wherein the blood glucose response model is an artificial intelligence model or a hybrid model comprising a kinetic model and an artificial intelligence model.

3. The method according to claim 1, wherein a computer, a Smartphone or a glucose level monitor is used for storing personal blood glucose profile data and a blood glucose response model, tuning or training of the said model with the personal blood glucose profile data, and computing and displaying of the meal and/or the post-prandial exercise plans.

4. The method according to claim 1, wherein the meal comprises foods with low glycemic indices (GI) and low glycemic loads (GL), meeting the daily recommended carbohydrates and protein needs for said person.

5. The method according to claim 1, wherein the post-prandial blood glucose spike is reduced to be not more than 2 to 5 mmol/L above the pre-meal blood glucose level, or the glucose shock is reduced by at least 20% over that before following the method.

6. The method according to claim 1, wherein the post-prandial exercise plan includes body movement, forward or backward walking, forward or backward running, weight training, dancing, using a vibration machine, a tread mill, an elliptical machine or a rowing machine, spot running, stair climbing, or any other suitable form of physical activity.

7. The method according to claim 1, wherein the post-prandial exercise is performed by using a leg exercise machine that allows up and down, circular, or elliptical movement of the legs, or by using a vibration machine, each machine used while sitting on a chair at home or at work.

8. The method according to claim 1, wherein the post-prandial exercise is commenced at a time, t counted from the time the most recent significant meal has been taken, which falls between (tspike−x) and (tspike+y), where x is 10 to 30 minutes and y is 15 to 60 minutes.

9. The method according to claim 1, wherein at least one significant meal is taken semi-continuously by splitting the meal into more than one portion and taking each portion at a different time.

10. The method according to claim 1, wherein at least one significant meal is taken semi-continuously as a liquid by sipping it from a bottle.

11. The method according to claim 1, wherein the time, t, between two consecutive split meals is: 30 minutes<t minutes<120 minutes.

12. The method according to claim 1, wherein the tuned- or the trained-model-recommended meal and exercise plans are used without or with any alternative medicine or prescribed medicine, including insulin.

13. The method according to claim 1, wherein the blood glucose spike, or the glucose shock is reduced, thereby lowering the risk of developing obesity, or if already developed, managing obesity.

14. The method according to claim 1, wherein the blood glucose spike, or the glucose shock is reduced, thereby lowering the risk of developing abdominal fat, or if already developed, reducing abdominal fat.

15. The method according to claim 1, wherein the blood glucose spike, or the glucose shock is reduced, thereby lessening hair loss.

16. The method according to claim 1, wherein the blood glucose spike, or the glucose shock is reduced, thereby lowering the risk of developing pre-diabetes, Type 2 diabetes, or managing pre-diabetes, Type 1 or Type 2 diabetes, or if already developed, managing the said diseases.

17. The method according to claim 1, wherein the blood glucose spike, or the glucose shock is reduced, thereby managing hypoglycemia.

18. The method according to 1, wherein the blood glucose spike, or the glucose shock is reduced, thereby assuaging aging-associated cognitive decline or dementia, or lowering the risk of developing Alzheimer's disease.

19. The method according to claim 1, wherein the blood glucose spike, or the glucose shock is reduced, thereby lowering the risk of developing cardiovascular diseases, nephropathy, neuropathy, retinopathy, or cancer.

* * * * *